United States Patent
Drmanac

(10) Patent No.: US 6,309,824 B1
(45) Date of Patent: *Oct. 30, 2001

(54) METHODS FOR ANALYZING A TARGET NUCLEIC ACID USING IMMOBILIZED HETEROGENEOUS MIXTURES OF OLIGONUCLEOTIDE PROBES

(75) Inventor: Radoje T. Drmanac, Palo Alto, CA (US)

(73) Assignee: Hyseq, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/784,747

(22) Filed: Jan. 16, 1997

(51) Int. Cl.$^7$ .............................. C12Q 1/68; C07H 21/04; C12P 19/34
(52) U.S. Cl. ..................... 435/6; 435/91.5; 435/91.52; 536/24.3; 536/24.31; 536/24.32
(58) Field of Search ................... 435/6, 91.5, 91.52; 436/501, 94; 536/24.31, 24.32, 24.3

(56) References Cited

U.S. PATENT DOCUMENTS

| | | |
|---|---|---|
| 4,562,159 | 12/1985 | Shafritz . |
| 4,613,566 | 9/1986 | Potter . |
| 4,677,054 | 6/1987 | White et al. . |
| 4,731,325 | 3/1988 | Palva et al. . |
| 4,766,062 | 8/1988 | Diamond et al. . |
| 4,849,334 | 7/1989 | Lorinez . |
| 4,882,269 * | 11/1989 | Schneider ............................ 435/6 |
| 4,883,750 | 11/1989 | Whiteley . |
| 4,981,783 | 1/1991 | Augenlicht . |
| 5,002,867 | 3/1991 | Macevicz . |
| 5,202,231 | 4/1993 | Drmanac . |
| 5,310,893 | 5/1994 | Erlich et al. . |
| 5,348,855 | 9/1994 | Dattagupta et al. . |
| 5,436,327 | 7/1995 | Southern et al. . |
| 5,492,806 | 2/1996 | Drmanac . |
| 5,503,980 * | 4/1996 | Cantor ................................... 435/6 |
| 5,545,531 | 8/1996 | Rava . |
| 5,807,522 * | 9/1998 | Brown et al. ........................ 422/50 |
| 5,837,832 * | 11/1998 | Chee et al. ........................ 536/22.1 |

FOREIGN PATENT DOCUMENTS

| | | |
|---|---|---|
| 0 202 758 A1 | 4/1986 | (EP) . |
| 3506703 C1 | 4/1986 | (DE) . |
| 0200113A2 | 11/1986 | (EP) . |
| 0 228 075 A2 | 12/1986 | (EP) . |
| 0205532B1 | 12/1986 | (EP) . |
| 0 235 726 A3 | 9/1987 | (EP) . |
| 0238332A2 | 9/1987 | (EP) . |
| 0 281 927 A3 | 9/1988 | (EP) . |
| 0373203B1 | 6/1990 | (EP) . |
| 0392546A2 | 10/1990 | (EP) . |
| 0 197 266 B1 | 7/1991 | (EP) . |
| 0 237 362 B1 | 3/1992 | (EP) . |
| 0514927A1 | 11/1992 | (EP) . |
| WO 85/01051 | 3/1985 | (WO) . |
| WO 86/03782 | 7/1986 | (WO) . |
| WO 88/01302 | 2/1988 | (WO) . |
| WO 88/10313 | 12/1988 | (WO) . |
| WO 39/11548 | 11/1989 | (WO) . |
| WO 89/10977 | 11/1989 | (WO) . |
| WO 89/11548 | 11/1989 | (WO) . |

(List continued on next page.)

OTHER PUBLICATIONS

Bainst, W., and Smith, G.C., (1988), "A Novel Method for Nucleic Acid Sequence Determination," Journal of Theoretical Biology, 135: 303–307.

Beltz, G.A., Jacobs, K.A., Eickbush, T.H., Cherbas, P.T., and Kafatos, F.C., (1983), "Isolation of Multigene Families and Determination of Homologies by Filter Hybridization Methods," Methods in Enzymology, 100(19), 266–285.

Conner, B.J., Reyes, A.A., Morin, C., Itakura, K., Teplitz, R.L., and Wallace, R.B., (1983) "Detection of Sickle Cell $\beta^s$–globin Allele by Hybridization with Synthetic Oligonucleotides," Proc. Natl. Acad. Sci. USA, 80, 278–282.

Hobden, A.N., Read, M.J., Dykes, C.W., and Harford, S., (1984), "M13 Clones Carrying Point Mutations: Identification by Solution Hybridization," Analytical Biochemistry, 144, 75–78.

Matthews, J.A., Kricka, L.J., (1988), "Analytical Strategies for the Use of DNA Probes," Review Article, Analytical Biochemistry, 169, 1–25.

Meinkoth, J., and Wahl, G., (1984), "Hybridization of Nucleic Acids Immobilized on Solid Supports," Review Article, Analytical Biochemistry, 138, 267–284.

Poustka, A., Phol, T., Barlow, D.P., Zehetner, G., Craig, A., Michiels, F., Ehrich, E., Frischauf, A.M., and Lehrach, H., (1986), "Molecular Approaches to Mammalian Genetics," Cold Spring Harbor Symposia on Quantitative Biology, LI, 131–139.

(List continued on next page.)

Primary Examiner—Carla J. Myers
(74) Attorney, Agent, or Firm—Marshall, Gerstein, & Borun

(57) ABSTRACT

The present invention provides a method for detecting a target nucleic acid species including the steps of providing an array of probes affixed to a substrate and a plurality of labeled probes wherein each labeled probe is selected to have a first nucleic acid sequence which is complementary to a first portion of a target nucleic acid and wherein the nucleic acid sequence of at least one probe affixed to the substrate is complementary to a second portion of the nucleic acid sequence of the target, the second portion being adjacent to the first portion; applying a target nucleic acid to the array under suitable conditions for hybridization of probe sequences to complementary sequences; introducing a labeled probe to the array; hybridizing a probe affixed to the substrate to the target nucleic acid; hybridizing the labeled probe to the target nucleic acid; affixing the labeled probe to an adjacently hybridized probe in the array; and detecting the labeled probe affixed to the probe in the array.

18 Claims, No Drawings

FOREIGN PATENT DOCUMENTS

| | | |
|---|---|---|
| WO 90/03382 | 4/1990 | (WO) . |
| WO 90/04652 | 5/1990 | (WO) . |
| WO 92/10588 | 6/1992 | (WO) . |
| WO 93/04204 | 3/1993 | (WO) . |
| WO 94/27719 | 12/1994 | (WO) . |
| WO 95/09248 | 4/1995 | (WO) . |
| 9527078 * | 10/1995 | (WO) . |
| 9631622 * | 10/1996 | (WO) . |
| 6425 | 4/1987 | (YU) . |

OTHER PUBLICATIONS

Syvanen, A.C., (1986), "Nucleic Acid Hybridization: From Research Tool to Routine Diagnostic Method," Review Article, Medical Biology, 64, 313–324, Drmanac, R. Labat, I., Brukner, I., and Crkvenjakov, R., (1989), "Sequencing a Megabase Plus DNA by Hybridization: Theory of the Method," Genomics, 4, 114–128.

Gusev, V.D., Kulichkov, V.A., and Titkova, T.N., (1980), "Analysis of Genetic Texts. I. 1–Gram Characteristics," Emperical Prediction and Recognition of Patterns, 83, 11–33.

Saiki, R.K., Walsh, P.S., Levenson, C.H., Erlich, H.A., (1989), "Genetic Analysis of Amplified DNA with Immobilized Sequence–Specific Oligonucleotide Probes," Proc. Natl. Acad. Sci. USA, 86, 6230–6234.

Drmanac, R., Labat, I., Strezoska, Z., Paunesku, T., Radosavljevic, D., Drmanac, S., and Crkvenjakov, R., (1990), "Sequencing by Oligonucleotide Hybridization: A Promising Framework in Decoding of the Genome Program?," Research Article, p.47–59.

Besmer, P., Miller Jr., R.C., Caruthers, M.H., Kumar, A., Minamoto, K., Van De Sande, J.H., Sidarova, N., and Khorana, H.G., (1972), "Hybridization of Polydeoxynucleotides with Tyrosine Transfer RNA Sequences to the r–Strand of $\phi 80$ psu$^{+///}$ DNA," J. Mol. Biol., 72, 503–522.

Breslauer, K.J., Frank, R., Blocker, H., and Marky, L.A., (1986), "Predicting DNA Duplex Stability from the Base Sequence," Proc. Natl. Acad. Sci., 83, 3746–3750.

Craig, M.E., Crothers, D.M., and Doty, P., (1971), "Relaxation Kinetics of Dimer Formation by Self Complementary Oligonucleotides," J. Mol. Biol., 62, 383–401.

Craig, A.G., Nizetic, D., Hoheisel, J.D., Zehetner, G. and Lehrach, H., (1990), "Ordering of Cosmid Clones Covering the Herpes Simplex Virus Type 1 (HSV–I): A Test Case for Fingerprinting by Hybridisation," Nucleic Acids Research, 18(9), 2653–2660.

Drmanac, R., Lennon, G., Drmanac, S., Labat, I., Crkvenjakov, R., and Lehrach, H., (1990), "Partial Sequencing by Oligo–Hybridization: Concept and Applications in Genome Analysis," The First International Conference on Electrophoresis, Supercomputing and the Human Genome, pp. 66–70.

Gilliam, S., Waterman, K., and Smith, M., (1975), "The Base–Pairing Specificity of Cellulose–pdT$_9$," Nucleic Acids Research, 2(5), 625–634.

Ikuta, S., Takagi, K., Wallace, R.B., and Itakura, K., (1987), "Dissociation Kinetics of 19 Base Paired Oligonucleotide–DNA Duplexes Containing Different Single Mismatched Base Pairs," Nucleic Acids Research, 15(2) 797–811.

Khrapko, K.R., Lysov, Y.P., Khorlyn, A.A., Shick, V.V., Florentiev, V.L., and Mirzabekov, A.D., (1989), "An Oligonucleotide Hybridization Approach to DNA Sequencing," Febs Letters, 256(1,2) 118–122.

Kohara, Y., Akiyama, K., and Isono, K., (1987), "The Physical Map of the Whole *E. coli* Chromosome: Application of a New Strategy for Rapid Analysis and Sorting of a Large Genomic Library," 50, 495–508.

Lewin, R., (1986), "Proposal to Sequence the Human Genome Stirs Debate," Research News, Molecular Biology of *Homo Sapians*, 232, 1598–1600.

Craig, A., Michiels, F., Zehetner, G., Sproat, B., Burmeister, M., Bucan, M., Poustka, A., Pohl, T., Frischauf, A.M., Lehrach, H., (1987), "Molecular Techniques to Mammalian Genetics: A New Era in Genetic Analysis," Human Genetics, pp. 126–132.

Wallace, R.B., Shaffer, J., Murphy, R.F., Bonner, J., Hirose, T., and Itakura, K., (1979), "Hybridization of Synthetic Oligodeoxyribonucleotides to $\phi_x$ 174 DNA: The Effect of Single Base Pair Mismatch," Nucleic Acids Research, 6(11) 3543–3557.

Wallace, R.B., Johnson, M.J., Hirose, T., Miyake, T., Kawashima, E.H., and Itakura, K., (1981), "The Use of Synthetic Oligonucleotides as Hybridization Probes, II. Hybridization of Oligonucleotides of Mixed Sequence to Rabbit $\beta$–Globin DNA," Nucleic Acids Research, 9(4) 879–894.

Wetmur, J.G., Davidson, N., (1968), "Kinetics of Renaturation of DNA," J. Mol. Biol., 31, 349–370.

Wetmur, J.G., (1976), "Hybridization and Renaturation Kinetics of Nucleic Acids," Annual Review of Biophysics and Bioengineering, 5, 337–361.

Wood, W.I., Gitschier, J., Lasky, L.A., and Lawn, R.M., (1985), "Base Composition–Independent Hybridization in Tetramethylammonium Chloride: A Method for Oligonucleotide Screening of Highly Complex Gene Libraries," Proc. Natl. Acad. Sci. USA, 82, 1585–1588.

Angelini, G., De Preval, C., Gorski, J., and Mach, B., (1986), "High–Resolution Analysis of Human HLA–DR Polymorphism by Hybridization with Sequence–Specific Oligonucleotide Probes," Proc. Natl. Acad. Sci. USA, 83, 4489–4493.

Berdoz, J., Gorski, Jack, Termijtelen, A.M., Dayer, J.M., Irle, C., Schendel, D., Mach, B., (1987), "Constitutive and Induced Expression of the Individual HLA–DR $\beta$ and $\alpha$ Chain Loci in Different Cell Types," The Journal of Immunology, 139(4), 1336–1341.

Bugawan, T.L., Horn, G.T., Long, C.M., Mickelson, E., Hansen, J.A., Ferrara, G.B., Angeline, G., and Erlich, H.A., (1988), "Analysis of HLA–DP Allelic Sequence Polymorphism Using the in Vitro Enzymatic NDA Amplification of DP–$\alpha$ and DP–$\beta$ Loci," Journal of Immunology, 141(12), 4024–4030.

Church, G.M., and Gilbert, W., (1983), "Genomic Sequencing,", Proc. Natl. Acad. Sci., 81, 1991–1995.

Crkvenjakov, R., Bucan, M., Konstantinovic, M., Fogel, M., Savic, A., and Glisin, V., (1984), "Characterization of Two Rat Globin cDNA Clones," Hemoglobin, 8(6), 597–611.

Crkvenjakov, R., Drmanac, R., Bucan, M., Konstantinovic, M., Fogel, M., Maksimovic, V., Petrovic, N., Savic, A., and Glisin, V., (1984), "Cloning of Eucaryotic Gene Sequences: Studies on Human Fibroblast Interferon and Rat Globin Genes," Periodicum Biologorum, 86(2) 115–124.

Gorski, J., Tilanus, M., Giphart, M., and Mach, B., (1987), "Oligonucleotide Genotyping Shows that Alleles at the HLA–DR III Locus of the DRw52 Supertypic Group Segregate Independently of Known DR or Dw Specificities," Immunogenetics, 25, 79–83.

Irle, C., Jaques, D., Tiercy, J.M., Fuggle, S.V., Gorski, J., Termijtelen, A., Jeannet, M., and Mach, B., (1988), "Functional Polymorphism of Each of the Two HLA–DR β Chain Loci Demonstrated with Antigen–Specific DR3– and Drw52–Restricted T Cell Clones," J. Exp. Med., 167, 853–872.

Landry, M.D., M.L., Fong, PhD., C.K.Y., (1985), "Nucleic Acid Hybridization in the Diagnosis of Viral Infections," Clinics in Laboratory Medicine, 5(3), 513–529.

Lehrach, H., Zehetner, G., Nicetic, D., Craig, A., Michiels, F., (1988), "Oligonucleotide Fingerprinting, A Parallel Approach to Establish Ordered Clone Libraries," Abstracts and Papers presented at the 1988 meeting on Genome Mapping and Sequencing, p.11.

Lehrach, H., Drmanac, R., Hoheisel, J., Larin, Z., Lennon, G., Monaco, A.P., Nizetic, D., Zehetner, G., and Poustka, A., (1990), "Hybridization Fingerprinting in Genome Mapping and Sequencing," Genome Analysis, 1, 39–71.

Michiels, F., Craig, A.G., Zehetner, G., Smith, G.P., and Lehrach, H., (1987), "Molecular Approaches to Genome Analysis: A Strategy for the Construction of Ordered Overlapping Clone Libraries," Cabios: Molecular Analysis of Genetic Distances, 3(3), 203–210.

Pevzner, P.A., (1989), "1–Tuple DNA Sequencing: Computer Analysis," Journal of Biomolecular Structure & Dynamics, 7(1), 63–73.

Rappold, G.A., Stubbs, L., Labeit, S., Crkvenjakov, R.B., and Lehrach, H., (1987), "Identification of a Testis–Specific Gene from the Mouse T–Complex Next to a CpG–rich Island," The EMBO Journal, 6(7), 1975–1980.

Saiki, R.K., Scharf, S., Faloona, F., Mullis, K.B., Horn, G.T., Erlich, H.A., Arnheim, N., (1985), "Enzymatic Amplification of β–Globin Genomic Sequences and Restriction Site Analysis for Diagnosis of Sickle Cell Anemia," Science: Research Article, 230, 1350–1354.

Saiki, R.K., Bugawan, T.L., Horn, G.T., Mullis, K.B., and Erlich, H.A., (1986), "Analysis of Enzymatically Amplified β–Globin and HLA–DQα DNA with Allele–Specific Oligonucleotide Probes," Letters to Nature, 324, 163–166.

Saiki, R.K., Walsh, P.S., Levenson, C.H., and Erlich, H.A., (1989), "Genetic Analysis of Amplified DNA with Immobilized Sequence–Specific Oligonucleotide Probes," Proc. Natl. Acad. Sci. USA, 86, 6230–6234.

Scharf, S.J., Friedman, A., Brautbar, C., Szafer, F., Steinman, L., Horn, G., Gyllensten, U., and Erlich, H.A., (1988), "HLA Class II Allelic Variation and Susceptibility to *Pemphigus Vulgaris*," Proceedings of Natl. Academy of Science, 85, 3504–3508.

Staden, R., (1980), "A New Computer Method for the Storage and Manipulation of DNA Gel Reading Data," Nucleic Acid Research, 8, 3673–3695.

Stevanovic, M., Paunesku, T., Radosavljevic, D., Drmanac, R., and Crkvenjakov, R., (1989), "Variant Chromosomal Arrangement of Adult β–Globin Genes in Rat," Genetics, 79, 139–150.

Sterc, J., and Novakova, V., (1988), "Role of the Limbic System in the Regulation of the Maternal Behavior in Laboratory Rats," Journal of Experimental Animal Science: XXIVth International Symposium, p.192.

Termijtelen, A., Gorski, J., Robbins, F.M., Tanigaki, N., Tosi, R., Tilanus, M.G.J., Schroeijers, W.E.M., and Van Rood, J.J., (1988) "Correlations Between Polymorphisms at the DNA and at the Protein Level of Drw52 Hapoltypes, Revealed with a Variety of Techniques," Human Immunology, 22, 171–178.

Thein, S.L., and Wallace, R.B., (1986), "The Use of Synthetic Oligonucleotides as Specific Hybridization Probes in the Diagnosis of Genetic Disorders," Human Genetic Diseases: A Practical Approach, Ch. 3, 33–50.

Tiercy, J.M., Gorski, J., Jeannet, M., and Mach, B., (1988), "Identification and Distribution of Three Serologically Undetected Alleles of HLA–DR by Oligonucleotide DNA Typing Analysis," Proc. Natl. Acad. Sci. USA, 85, 198–202.

Ucla, C., Van Rood, J.J., Gorski, J., and Mach, B., (1987), "Analysis of HLA–D Micropolymorphism by a Simple Procedure: RNA Oligonucleotide Hybridization," J. Clin. Invest., 80, 1155–1159.

Wu, D.Y., Nozari, G., Schold, M., Conner, B.J., and Wallace R.B., (1989), "Direct Analysis of Single Nucleotide Variation in Human DNA and RNA Using In Situ Dot Hybridization," Laboratory Methods: DNA, 8(2) 135–142.

Schildkraut, C.L., Marmur, J., and Doty, P., (1961), "The Formation of Hybrid DNA Moleculres and Their Use in Studies of DNA Homologies," J. Mol. Biol., 8, 595–617.

Suggs, S.V., Wallace, R.B, Hirose, T., Kawashima, E.H., and Itakura, K., (1981), "Use of Synthetic Oligonucleotides as Hybridization Probes: Isolation of Cloned cDNA Sequences for Human $β_2$–Microglobulin," Proc. Natl. Acad. Sci. USA, 78(11) 6613–6617.

Evans, G.A., and Lewis, K.A., (1989), "Physical Mapping of Complex Genomes by Cosmid Multiplex Analysis," Proc. Natl. Acad. Sci. USA, 86, 5030–5034.

Sim, G.K., Kafatos, F.C., Jones, C.W., and Koehler, M.D., (1979), "Use of cDNA Library for Studies on Evolution and Development Expression of the Chorion Multigene Families," Cell, pp. 1303–1316.

Stein, S.K.,(1961), "The Mathematician as an Explorer," Scientific American, 204, 149–158.

Labat, I., (1988), "Subfragments as an Informative Characteristic of the DNA Molecule–Computer Simulation," Research Report, pp. 1–33.

(1988), "Sequencing of Megabase Plus DNA by Hybridization: Theory of the Method," A poster presented at the 1988 Meeting on Genome Mapping and Sequencing, pp. III–IV.

Masiakowski et al., (1982), Cloning of cDNA Sequences of Hormone–Regulated Genes from the MCF–7 Human Breast Cancer, Nucleic Acids Research, 10(24), 7895–7903.

Lysov, et al., (1988), Determination of the DNA Nucleotide Sequence by the Hybridization with Oligonucleotides, A new method (in Russian), Doklady Akademii Nauk SSSR, 303(5), 1508–1511.

(1996) Nature Genetics, 14(4), 367–370.

Besmer, P., Miller, R. J., Caruthers, M. H., Kumar, A., Minamoto, K., Van de Sande, J. H., Sidarova, N., and Khorana, H. G. (1972). "Studies on Polynucleotides. CXVII. Hybridization of Polydeoxynucleotides with Tyrosine Transfer RNA Sequences to the r–Strand of 100 80psu + III DNA." J Mol Biol, 72, 503–22.

Blanchard, A. P., Kaiser, R. J., and Hood, L. E. (1996). "High Density Oligonucleotide Arrays." Biosensors and Bioelectronics, 11(6/7), 687–690.

Blanchard, A. P., and Hood, L. (1996), "Sequence to array: Probing the Genome's Secrets." Nature Biotechnology, 14, 1649.

Broude, N. E., Sano, T. Smith, C. L., and Cantor, C. R. (1994). "Enhanced DNA Sequencing by Hybridization Workshop." Genomics, 13, 1378–83.

Chee, M., Yang, R., Hubbell, E., Berno, A., Huang, X. C., Stern, D., Winkler, J., Lockhart, D. J., Morris, M. S., and Fodor, S. P. (1996). "Accessing Genetic Information with High–Density DNA Arrays." Science, 274, 610–4.

Church, G. M., and Kieffer–Higgins, S. (1988). "Multiplex DNA Sequencing." Science, 240, 185–8.

Drmanac, R., Labat, I., Brukner, I., and Crkvenjakov, R. (1989). "Sequencing of Megabase Plus DNA by Hybridization: Theory of the Method." Genomics, 4, 114–28.

Drmanac, R., Labat, I., Strezoska, Z., and Crkvenjakov, R. (1989). "An Alternative Large DNA Sequencing Method: The Theoretical and Informational Feasability of Sequencing by Hybridization." Abstracts of papers presented at the 1989 meeting of Genome Mapping and Sequencing: Apr. 26–Apr. 30, 1989, C. Cantor, M. Olson, and R. Roberts, ed., Cold Spring Harbor Laboratory, Cold Spring Harbor, 44.

Drmanac, R., Strezoska, Z., Labat, I., Drmanac, S., and Crkvenjakov, R. (1990). "Reliable Hybridization of Oligonucleotides as Short as Six Nucleotides." DNA Cell Biol, 9(7), 527–34.

Drmanac, R., and Crkvenjakov, R. (1990). "Prospects for a Miniaturized, Simplified, and Frugal Genome Project." Scientia Yugoslavica, 16(1–2), 97–107.

Drmanac, R., Lennon, G., Drmanac, S., Labat, I., Crkvenjakov, R., and Lehrach, H. (1990). "Partial Sequencing by Oligo–Hybridization: Concept and Applications in Genome Analysis." The First International Conference on Electrophoresis, Supercomputing and the Human Genome, C. Cantor and H. Lim, eds., World Scientific, Singapore, 60–74.

Drmanac, R., Labat, I., and Crkvenjakov, R. (1991). "An Algorithm for the DNA Sequence Generation from K–Tuple Word Contents of the Minimal Number of Random Fragments." J Biolmol Struct Dyn, 8(5), 1085–102.

Drmanac, R., Labat, I., Strezoska, Z., Paunesku, T., Radosavljevik, D., Drmanac, S., and Crkvenjakov, R. (1991). "Sequencing by Oligonucleotide Hybridization: a Promising Framework in Decoding of the Human Genome Program?" The First International Conference on Electrophoresis, Supercomputing and The Human Genome, Apr. 10–13, 1990, C. R. Cantor and H. A. Lim, eds., World Scientific, Singapore, 47–59.

Drmanac, R., Nizetic, D., Lennon, G. G., Beitverda, A., and Lehrach, H. (1991). "W (A or T) Sequences as Probes and Primers Suitable for Genomic Mapping and Fingerprinting." Nucleic Acids Res, 19(21), 5839–42.

Drmanac, R., Drmanac, S., Labat, I., Crkvenjakov, R., Vicentic, A., and Gemmell, A. (1992). "Sequencing by Hybridization: Towards an Automated Sequencing of One Million M13 Clones Arrayed on Membranes." Electrophoresis, 13, 566–73.

Drmanac, R., and Crkvenjakov, R. (1992). "Sequencing by Hybridization (SBH) with Oligonucleotide Probes as an Integral Approach for the Analysis of Complex Genomes." International Journal of Genome Research, 1(1), 59–79.

Drmanac, R. (1992). "How 1000 Base Pairs with 10% Error Become 10,000 Base Pairs of Correct Sequence: a Felicitious Marriage of the Gel and Hybridization Sequencing Methods." Abstracts of papers presented at the 1992 meeting on Genome Mapping and Sequencing: May 6–May 10, 1992, R. Myers, D. Porteous, and R. Roberts, eds., Cold Spring harbor Laboratory, Cold Spring Harbor, 318.

Drmanac, R., Drmanac, S., Strezoska, Z., Paunesku, T., Labat, I., Zeremski, M., Snoddy, J., Funkhouser, W. K., Koop, B., Hood, L., and et al. (1993) "DNA Sequence Determination by Hybridization: a Strategy for Efficient Large–Scale Sequencing [published erratum appears in Science Feb. 4, 1994;163(5147):596]." Science, 260, 1649–52.

Drmanac, R., Drmanac, S., Labat, I., Vicentic, A., Gemmell, A., Stavropoulos, N., and Jarvis, J. (1993). "SBH and the Integration of Complementary Approaches in the Mapping, Sequencing and Understanding of Complex Genomes." The Second International Conference on Bioinformatics, Supercomputing and Complex Genome Analysis: proceedings of the Jun. 4–7, 1992 Conference at St. Petersbug Beach, Florida, USA, H. A. Lim, J. W. Fickett, C. R. Cantor, and R. J. Robbins, eds., World Scientific, Singapore, 121–134.

Drmanac, S., and Drmanac, R. (1994). "Processing of cDNA and Genomic KiloBase–Size Clones for Massive Screening, Mapping and Sequencing by Hybridization." Biotechniques, 17(2), 328–9, 332–6.

Drmanac, R., Drmanac, S., Labat, I., and Stavropoulos, N. (1994). "Requirements in Screening cDNA Libraries for New Genes and Solutions Offered by SBH Technology." Identification of Transcribed Sequences, U. Hochgeschwender and K. Gardiner, eds., Plenum Press, New York, 239–251.

Drmanac, R., Drmanac, S., Jarvis, J., and Labat, I. (1994). "Sequencing by Hybridization." Automated DNA Sequencing and Analysis, M. D. Adams, C. Fields, and J. C. Venter, eds., Academic Press, Harcourt Brace & Company, London, 29–36.

Dyer, M., Frieze, A., and Suen S. (1994). "The Probability of Unique Solutions of Sequencing by Hybridization." J Comput Biol, 1(2), 105–10.

Gillam, S., Waterman, K., and Smith, M. (1975). "The Base–Pairing Specificity of Cellulose–pdT9." Nucleic Acids Res, 2(5), 625–34.

Gingeras, T. R., Kwoh, D. Y., and Davis, G. R. (1987). "Hybridization Properties of Immobilized Nucleic Acids." Nucleic Acids Res, 15(13), 5373–90.

Hacia, J. G., Brody, L. C., Chee, M. S., Fodor, S. P., and Collins, F. S. (1996). "Detection of Heterozygous Mutations in BRCA1 Using High Density Oligonucleotide Arrays and Two–Colour Fluorescence Analysis [see comments]." Nat Genet, 14, 441–7.

Khrapko, K. R., Lysov Yu, P., Khorlyn, A. A., Shick, V. V., Florentiev, V. L., and Mirzabekov, A. D. (1989). "An Oligonucleotide Hybridization Approach to DNA Sequencing." FEBS Lett, 256 (1–2), 118–22.

Kozal, M. J., Shah, N., Shen, N., Yang, R., Fucini, R., Merigan, T. C., Richman, D. D., Morris, D., Hubbell, E., Chee, M., and Gingeras, T. R. (1996). "Extensive Polymorphisms Observed in HIV–1 Clade B Protease Gene using High–Density Oligonucleotide Arrays." Nat Med, 2(7), 753–9.

Kreiner, T. (1996). "Rapid Genetic Sequence Analysis Using a DNA Probe Array System." American Laboratory, Mar., 39–43.

Labat, I., and Drmanac, R. (1993). "Simulations of Ordering and Reconstruction of Random DNA Clones Hybridized with a Small Number of Oligomeric Probes." The Second International Conference on Bioinformatics, Supercomputing and Complex Genome Analysis: proceedings of the Jun. 4–7, 1992 Conference at St. Petersburg Beach, Florida, USA, H. A. Lim, J. W. Fickett, C. R. Cantor, and R. J. Robbin, eds., World Scientific, Singapore, 555–565.

Latham, T., and Smith, F. I. (1989). "Detection of Single–Base Mutations in DNA Molecules Using the Solution Melting Method." DNA, 8(3), 223–31.

Lehrach, H., Drmanac, R., Hoheisel, J., Larin, Z., Lennon, G., Nizetic, D., Monaco, T., Zehetner, G., and Poustka, A., "Hybridization Fingerprinting in Genome Mapping and Sequencing." Genome Analysis I, Genetic and Physical Mapping, Cold Spring Harbor, 39–81.

Lipshutz, R. J. (1993). "Likelihood DNA Sequencing by Hybridization." J Biomol Struct Dyn, 11(3), 637–53.

Lipshutz, R. J., Morris, D., Chee, M., Hubbell, E., Kozal, M. J., Shah, N., Shen, N., Yang, R., and Fodor, S. P. (1995). "Using Oligonucleotide Probe Arrays to Access Genetic Diversity." Biotechniques, 19(3), 442–7.

Lockhart, D. J., Dong, H., Byrne, M. C., Follettie, M. T., Gallo, M. V., Chee, M. S., Mittman, M., Wang, C., Kobayashi, M., Horton, H., and Brown, E. L. (1996). "Expression Monitoring by Hybridization to High Density Oligonucleotide Arrays." Nature Biotechnology, 14, 1675–80.

Lysov Iu, P., Florent'ev, V. L., Khorlin, A. A., Khrapko, K. R., and Shik, V. V. (1988). "Determination of the Nucleotide Sequence of DNA Using Hybridization with Oligonucleotides. A New Method," Dokl Akad Nauk SSSR, 303(6), 1508–11.

Mirzabekov, A. D. (1994). "DNA Sequencing by Hybridization—A Megasequencing Method and A Diagnostic Tool?" Trends Biotechnol, 12, 27–32.

Paunesku, T., Gemmell, M. A., Crkvenjakov, R., and Woloschak, G. E. (1994). "A Presumed B6 Strain–Specific p53 Polymorphism is Confined to a B6 Cell Line and Is Likely to Represent a Facilitating Mutation." Mamm Genome, 5, 106–7.

Pevzner, P. A., Lysov, Yu, P., Khrapko, K. R., Belyavsky, A. V., Florentiev, V. L., and Mirzabekov, A. D. (1991). "Improved Chips for Sequencing by Hybridization." J Biomol Struct Dyn, 9(2), 399–410.

Prober, J. M., Trainor, G. L., Dam, R. J., Hobbs, F. W., Robertson, C. W., Zagursky, R. J., Cocuzza, A. J., Jensen, M. A., and Baumeister, K. (1987). "A System for Rapid DNA Sequencing with Fluorescent Chain–Terminating Dideoxynucleotides." Science, 238, 336–41.

Shoemaker, D. D., Lashkari, D. A., Morris, D., Mittman, M., and Davis, R. W. (1996). "Quantitative Phenotypic Analysis of Yeast Deletion Mutants Using a Highly Parallel Molecular Bar–Coding Strategy [see comments]." Nat Genet, 14, 450–6.

Smith, L. M., Sanders, J. Z., Kaiser, R. J., Hughes, P., Dodd, C., Connell, C. R., Heiner, C., Kent, S. B., and Hood, L. E. (1986). "Fluorescence Detection in Automated DNA Sequence Analysis." Nature, 321, 674–9.

Strezoska, Z., Paunesku, T., Radosavljevic, D., Labat, I., Drmanac, R., and Crkvenjakov, R. (1991). "DNA Sequencing by Hybridization: 100 Bases Read by a Non–Gel–Based Method." Proc Natl Acad Sci U S A, 88, 10089–93.

Urdea, M. S., Running, J. A., Horn, T., Clyne, J., Ku, L. L., and Warner, B. D. (1987). "A Novel Method for the Rapid Detection of Specific Nucleotide Sequences in Crude Biological Samples without Blotting or Radioactivity; Application to the Analysis of Hepatitis B Virus in Human Serum." Gene, 61, 253–64.

* cited by examiner

METHODS FOR ANALYZING A TARGET NUCLEIC ACID USING IMMOBILIZED HETEROGENEOUS MIXTURES OF OLIGONUCLEOTIDE PROBES

FIELD OF THE INVENTION

This invention relates in general to methods and apparatus for nucleic acid analysis, and, in particular, to methods and apparatus for DNA analysis.

BACKGROUND

The rate of determining the sequence of the four nucleotides in DNA samples is a major technical obstacle for further advancement of molecular biology, medicine, and biotechnology. Nucleic acid sequencing methods which involve separation of DNA molecules in a gel have been in use since 1978. The other proven method for sequencing nucleic acids is sequencing by hybridization (SBH).

The traditional method of determining a sequence of nucleotides (i.e., the order of the A, G, C and T nucleotides in a sample) is performed by preparing a mixture of randomly-terminated, differentially labelled DNA fragments by degradation at specific nucleotides, or by dideoxy chain termination of replicating strands. Resulting DNA fragments in the range of 1 to 500 bp are then separated on a gel to produce a ladder of bands wherein the adjacent samples differ in length by one nucleotide.

The array-based approach of SBH does not require single base resolution in separation, degradation, synthesis or imaging of a DNA molecule. Using mismatch discriminative hybridization of short oligonucleotides K bases in length, lists of constituent K-mer oligonucleotides may be determined for target DNA. DNA sequence for the target DNA may be assembled by uniquely overlapping several oligonucleotides.

There are several approaches available to achieve sequencing by hybridization. In a process called SBH Format 1, DNA samples are arrayed, and labeled probes are hybridized with the samples. Replica membranes with the same sets of sample DNAs may be used for parallel scoring of several probes and/or probes may be multiplexed. DNA samples may be arrayed and hybridized on nylon membranes. Each membrane array may be reused many times. Format 1 is especially efficient for batch processing large numbers of samples.

In SBH Format 2, probes are arrayed at location on a substrate which correspond to their respective sequences, and a labeled DNA sample fragment is hybridized to the arrayed probes. In this case, sequence information about a fragment may be determined in a simultaneous hybridization reaction with all of the arrayed probes. For sequencing other DNA fragments, the same oligonucleotide array may be reused. The arrays may be produced by spotting or by in situ synthesis of probes.

In Format 3 SBH, two sets of probes are used. One set may be in the form of arrays of probes with known positions, and another, labeled set may be stored in multiwell plates. In this case, target DNA need not be labelled. Target DNA and one or more labelled probes are added to the arrayed sets of probes. If one attached probe and one labelled probe both hybridize contiguously on the target DNA, they are covalently ligated, producing a detected sequence equal to the sum of the length of the ligated probes. The process allows for sequencing long DNA fragments, e.g. a complete bacterial genome, without DNA subcloning in smaller pieces.

In the present invention, SBH is applied to the efficient identification and sequencing of one or more DNA samples. The procedure has many applications in DNA diagnostics, forensics, and gene mapping. It also may be used to identify mutations responsible for genetic disorders and other traits, to assess biodiversity and to produce may other types of data dependent on DNA sequence.

SUMMARY OF THE INVENTION

The present invention provides a method for detecting a target nucleic acid species including the steps of providing an array of probes affixed to a substrate and a plurality of labeled probes wherein each labeled probe is selected to have a first nucleic acid sequence which is complementary to a first portion of a target nucleic acid and wherein the nucleic acid sequence of at least one probe affixed to the substrate is complementary to a second portion of the nucleic acid sequence of the target, the second portion being adjacent to the first portion; applying a target nucleic acid to the array under suitable conditions for hybridization of probe sequences to complementary sequences; introducing a labeled probe to the array; hybridizing a probe affixed to the substrate to the target nucleic acid; hybridizing the labeled probe to the target nucleic acid; affixing the labeled probe to an adjacently hybridized probe in the array; anddetecting the labeled probe affixed to the probe in the array. According to preferred methods of the invention the array of probes affixed to the substrate comprises a universal set of probes. According to other preferred aspects of the invention at least two of the probes affixed to the substrate define overlapping sequences of the target nucleic acid sequence and more preferrably at least two of the labelled probes define overlapping sequences of the target nucleic acid sequences. In this manner a overlapping probes can confirm the sequence of the sample nucleic acid. The invention also provides a method of determining expression of a member of a set of partially or completely sequenced genes in a cell type, a tissue or a tissue mixture comprising the steps of: defining pairs of fixed and labeled probes specific for the sequenced gene; hybridizing unlabeled nucleic acid sample and corresponding labeled probes to one or more arrays of fixed probes; forming covalent bonds between adjacent hybridized labeled and fixed probes; removing unligated probes; and determining the presence of the sequenced gene by detection of labeled probes bound to prespecified locations in the array. Finally, according to a further aspect of the invention a method is provided of detecting the presence of an infectious agent characterized by a target nucleic acid sequence comprising the steps of: contacting a nucleic acid sample with a set of immobilized oligonucleotide probes attached to a solid substrate under hybridizing conditions wherein said first set of probes are capable of specific hybridization with different portions of said target nucleic acid sequence; contacting said sample with a set of labelled oligonucleotide probes in solution under hybridizing conditions wherein said second set of probes are capable of specific hybridization with different portions of said target nucleic acid sequence adjacent the first set of probes; ligating the immobilized probes and labelled probes that are immediately adjacent on a target sequence with a ligase; removing any non-ligated labelled probes; detecting the presence of said infectious agent by detecting the presence of said labelled probe.

DETAILED DESCRIPTION

Format 1 SBH is appropriate for the simultaneous analysis of a large set of samples. Parallel scoring of thousands of samples on large arrays may be performed are in thousands of independent hybridization reactions using small pieces of membranes. The identification of DNA may involve 1–20 probes per reaction and the identification of mutations may in some cases involve more than 1000 probes specifically selected or designed for each sample. For identification of the nature of the mutated DNA segments, specific probes may be synthesized or selected for each mutation detected in the first round by hybridizations.

DNA samples may be prepared in small arrays which may be separated by appropriate spacers, and which may be simultaneously tested with probes selected from a set of oligonucleotides which may be arrayed in multiwell plates. Small arrays may consist of one or more samples. DNA samples in each small array may include mutants or individual samples of a sequence. Consecutive small arrays may be organized into larger arrays. Such larger arrays may include replication of the same small array or may include arrays of samples of different DNA fragments. A universal set or probes includes sufficient probes to analyze a DNA fragment with prespecified precision, e.g. with respect to the redundancy of reading each base pair ("bp"). These sets may include more probes than are necessary for one specific fragment, but may include fewer probes than are necessary for testing thousands of DNA samples of different sequence.

DNA or allele identification and a diagnostic sequencing process may include the steps of:

1) Selection of a subset of probes from a dedicated, representative or universal set to be hybridized with each of a plurality small arrays;

2) Adding a first probe to each subarray on each of the arrays to be analyzed in parallel;

3) Performing hybridization and scoring of the hybridization results;

4) Stripping off previously used probes;

5) Repeating hybridization, scoring and stripping steps for the remaining probes which are to be scored;

5) Processing the obtained results to obtain a final analysis or to determine additional probes to be hybridized;

6) Performing additional hybridizations for certain subarrays; and

7) Processing complete sets of data and computing obtaining a final analysis.

This approach provides fast identification and sequencing of a small number of nucleic acid samples of one type (e.g. DNA, RNA), and also provides parallel analysis of many sample types in the form of subarrays by using a presynthesized set of probes of manageable size. Two approaches have been combined to produce an efficient and versatile process for the determination of DNA identity, for DNA diagnostics, and for identification of mutations.

For the identification of known sequences, a small set of shorter probes may be used in place of a longer unique probe. In this approach, although there may be more probes to be scored, a universal set of probes may be synthesized to cover any type of sequence. For example, a full set of 6-mers includes only 4,096 probes, and a complete set of 7-mers includes only 16,384 probes.

Full sequencing of a DNA fragment may be performed with two levels of hybridization. One level is hybridization of a sufficient set of probes that cover every base at least once. For this purpose, a specific set of probes may be synthesized for a standard sample. The results of hybridization with such a set of probes reveal whether and where mutations (differences) occur in non-standard samples. To determine the identify of the changes, additional specific probes may be hybridized to the sample.

In another embodiment, all probes from a universal set may be scored. A universal set of probes allows scoring of a relatively small number of probes per sample in a two step process without an undesirable expenditure of time. The hybridization process may involve successive probings, in a first step of computing an optimal subset of probes to be hybridized first and, then, on the basis of the obtained results, a second step of determining additional probes to be scored from among those in a universal set.

In SBH sequence assembly, K-1 oligonucleotides which occur repeatedly in analyzed DNA fragments due to chance or biological reasons may be subject to special consideration. If there is no additional information, relatively small fragments of DNA may be fully assembled in as much as every base pair is read several times.

In the assembly of relatively longer fragments, ambiguities may arise due to the repeated occurrence in a set of positively-scored probes of a K-1 sequence (i.e., a sequence shorter than the length of the probe). This problem does not exist if mutated or similar sequences have to be determined (i.e., the K-1 sequence is not identically repeated). Knowledge of one sequence may be used as a template to correctly assemble a sequence known to be similar (e.g., by its presence in a database) by arraying the positive probes for the unknown sequence to display the best fit on the template.

The use of an array of sample arrays avoids consecutive scoring of many oligonucleotides on a single sample or on a small set of samples. This approach allows the scoring of more probes in parallel by manipulation of only one physical object. Subarrays of DNA samples 1000 bp in length may be sequenced in a relatively short period of time. If the samples are spotted at 50 subarrays in an array and the array is reprobed 10 times, 500 probes may be scored. In screening for the occurrence of a mutation, approximately 335 probes may be used to cover each base three times. If a mutation is present, several covering probes will be affected. The use of information about the identity of negative probes may map the mutation with a two base precision. To solve a single base mutation mapped with this precision, an additional 15 probes may be employed. These probes cover any base combination for two questionable positions (assuming that deletions and insertions are not involved). These probes may be scored in one cycle on 50 subarrays which contain a given sample. In the implementation of a multiple label color scheme (i.e., multiplexing), two to six probes, each having a different label such as a different fluorescent dye, may be used as a pool, thereby reducing the number of hybridization cycles and shortening the sequencing process.

In more complicated cases, there may be two close mutation or insertions. They may be handled with more probes. For example, a three base insertion may be solved with 64 probes. The most complicated cases may be approached by several steps of hybridization, and the selecting of a new set of probes on the basis of results of previous hybridizations.

If subarrays to be analyzed include tens or hundreds of samples of one type, then several of them may be found to contain one or more changes (mutations, insertions, or deletions). For each segment where mutation occurs, a specific set of probes may be scored. The total number of probes to be scored for a type of sample may be several hundreds. The scoring of replica arrays in parallel facilitates scoring of hundreds of probes in a relatively small number of cycles. In addition, compatible probes may be pooled. Positive hybridizations may be assigned to the probes selected to check particular DNA segments because these segments usually differ in 75% of their constituent bases.

By using a larger set of longer probes, longer targets may be conveniently analyzed. These targets may represent pools of shorter fragments such as pools of exon clones.

A specific hybridization scoring method may be employed to define the presence of heterozygotes (sequence variants) in a genomic segment to be sequenced from a diploid chromosomal set. Two variations are where: i) the sequence from one chromosome represents a basic type and the sequence from the other represents a new variant; or, ii) both chromosomes contain new, but different variants. In the first case, the scanning step designed to map changes gives a maximal signal difference of two-fold at the heterozygotic position. In the second case, there is no masking, but a more complicated selection of the probes for the subsequent rounds of hybridizations may be indicated.

Scoring two-fold signal differences required in the first case may be achieved efficiently by comparing corresponding signals with controls containing only the basic sequence type and with the signals from other analyzed samples. This approach allows determination of a relative reduction in the hybridization signal for each particular probe in a given sample. This is significant because hybridization efficiency may vary more than two-fold for a particular probe hybridized with different DNA fragments having the same full match target. In addition, heterozygotic sits may affect more than one probe depending upon the number of oligonucleotide probes. Decrease of the signal for two to four consecutive probes produces a more significant indication of heterozygotic sites. Results may be checked by testing with small sets of selected probes among which one or few probes selected to give a full match signal which is on average eight-fold stronger than the signals coming from mismatch-containing duplexes.

Partitioned membranes allow a very flexible organization of experiments to accommodate relatively larger numbers of samples representing a given sequence type, or many different types of samples represented with relatively small number of samples. A range of 4–256 samples can be handled with particular efficiency. Subarrays within this range of numbers of dots may be designed to match the configuration and size of standard multiwell plates used for storing and labelling oligonucleotides. The size of the subarrays may be adjusted for different number of samples, or a few standard subarray sizes may be used. If all samples of a type do not fit in one subarray, additional subarrays or membranes may be used and processed with the same probes. In addition, by adjusting the number of replicas for each subarray, the time for completion of identification or sequencing process may be varied.

Sequencing may be conducted by sequential hybridization with oligos. Alternatively, sets of oligos may be hybridized with unknown sequences simultaneously.

As used herein, "intermediate fragment" means an oligonucleotide between 5 and 1000 bases in length, and preferably between 10 and 40 bp in length.

In Format 3, a first set of oligonucleotide probes of known sequence is immobilized on a solid support under conditions which permit them to hybridize with nucleic acids having respectively complementary sequences. A labeled, second set of oligonucleotide probes is provided in solution. Both within the sets and between the sets the probes may be of the same length or of different lengths. A nucleic acid to be sequenced or intermediate fragments thereof may be applied to the first set of probes in double-stranded form (especially where a recA protein is present to permit hybridization under non-denaturing conditions), or in single-stranded form and under conditions which permit hybrids of different degrees of complementarity (for example, under conditions which discriminate between full match and one base pair mismatch hybrids). The nucleic acid to be sequenced or intermediate fragments thereof may be applied to the first set of probes before, after or simultaneously with the second set of probes. A ligase or other means of causing chemical bond formation between adjacent, but not between nonadjacent, probes may be applied before, after or simultaneously with the second set of probes. After permitting adjacent probes to be chemically bonded, fragments and probes which are not immobilized to the surface by chemical bonding to a member of the first set of probe are washed away, for example, using a high temperature (up to 100 degrees C) wash solution which melts hybrids. The bound probes from the second set may then be detected using means appropriate to the label employed (which may be chemiluminescent, fluorescent, radioactive, enzymatic or densitometric, for example).

Herein, nucleotide bases "match" or are "complementary" if they form a stable duplex by hydrogen bonding under specified conditions. For example, under conditions commonly employed in hybridization assays, adenine ("A") matches thymine ("T"), but not guanine ("G") or cytosine ("C"). Similarly, G matches C, but not A or T. Other bases which will hydrogen bond in less specific fashion, such as inosine or the Universal Base ("M" base, Nichols et al. 1994), or other modified bases, such as methylated bases, for example, are complementary to those bases for which they form a stable duplex under specified conditions. A probe is said to be "perfectly complementary" or is said to be a "perfectly match" if each base in the probe forms a duplex by hydrogen bonding to a base in the nucleic acid to be sequenced. Each base in a probe that does not form a stable duplex is said to be a "mismatch" under the specified hybridization conditions.

A list of probes may be assembled wherein each probe is a perfect match to the nucleic acid to be sequenced. The probes on this list may then be analyzed to order them in maximal overlap fashion. Such ordering may be accomplished by comparing a first probe to each of the other probes on the list to determine which probe has a 3' end which has the longest sequence of bases identical to the sequence of bases at the 5' end of a second probe. The first and second probes may then be overlapped, and the process may be repeated by comparing the 5' end of the second probe to the 3' end of all of the remaining probes and by comparing the 3' end of the first probe with the 5' end of all of the remaining probes. The process may be continued until there are no probes on the list which have not been overlapped with other probes. Alternatively, more than one probe may be selected from the list of positive probes, and more than one set of overlapped probes ("sequence nucleus") may begenerated in parallel. The list of probes for either such process of sequence assembly may be the list of all probes which are perfectly complementary to the nucleic acid to be sequenced or may be any subset thereof.

The 5' and 3' ends of sequence nuclei may be overlapped to generate longer stretches of sequence. Where ambiguities arise in sequence assembly due to the availability of alternative proper overlaps with probes or sequence nuclei, hybridization with longer probes spanning the site of overlap alternatives, competitive hybridization, ligation of alternative end to end pairs of probes spanning the site of ambiguity or single pass gel analysis (to provide an unambiguous framework for sequence assembly) may be used.

By employing the above procedures, one may obtain any desired level of sequence, from a pattern of hybridization (which may be correlated with the identity of a nucleic acid sample to serve as a signature for identifying the nucleic acid sample) to overlapping or non-overlapping probes up through assembled sequence nuclei and on to complete sequence for an intermediate fragment or an entire source DNA molecule (e.g. a chromosome).

Sequencing may generally comprise the following steps:

(a) contacting an array of immobilized oligonucleotide probes with a nucleic acid fragment under conditions effective to allow a fragment with a sequence complementary to that of an immobilized probe to form a primary complex with the immobilized probe such that the fragment has a hybridized and a non-hybridized portion;

(b) contacting a primary complex with a set of labeled oligonucleotide probes in solution under conditions effective to allow a primary complex including an unhybridized sequence complementary to that of a labeled probe to hybridize to the labeled probe, thereby forming a secondary complex wherein the fragment is hybridized with both an immobilized probe and a labeled probe;

(c) removing from a secondary complex any labeled probe that has not hybridized adjacent to an immobilized probe;

(d) detecting the presence of adjacent labeled and unlabeled probes by detecting the presence of the label; and (e) determining a nucleotide sequence of the fragment by connecting the known sequence of the immobilized and labeled probes.

Hybridization and washing conditions may be selected to detect substantially perfect match hybrids (such as those wherein the fragment and probe hybridize at six out of seven positions), or may be selected to permit detection only of perfect match hybrids by the use of more stringent hybridization conditions.

Suitable hybridization conditions may be routinely determined by optimization procedures or pilot studies. Such procedures and studies are routinely conducted by those skilled in the art to establish protocols for use in a laboratory. For example, conditions such as temperature, concentration of components, hybridization and washing times, buffer components, and their pH and ionic strength may be varied.

In embodiments wherein the labeled and immobilized probes are not physically or chemically linked, detection may rely solely on washing steps of controlled stringency. Under such conditions, adjacent probe remain hybridized due to a stability afforded by stacking interactions. Conditions may be varied to optimize the process as described above.

In embodiments wherein the immobilized and labeled probes are ligated, ligation may be implemented by a chemical ligating agent (e.g. water-soluble carbodiimide or cyanogen bromide). A ligase enzyme, such as the commercially available $T_4$ DNA ligase from $T_4$ bacteriophage, may be employed. The washing conditions which are selected to distinguish between adjacent versus nonadjacent labeled and immobilized probes are selected to make use of the difference in stability of continuously stacked or ligated adjacent probes.

Oligonucleotide probes may be labeled with fluorescent dyes, chemiluminescent systems, radioactive labels (e.g. $^{35}S$, $^{3}H$, $^{32}P$ or $^{33}P$) or with isotopes detectable by mass spectrometry.

Where a nucleic acid molecule of unknown sequence is longer than about 45 or 50 bp, the molecule may be fragmented and the sequences of the fragments determined. Fragmentation may be accomplished by restriction enzyme digestion, shearing or NaOH. Fragments may be separated by size (e.g. by gel electrophoresis) to obtain a preferred fragment length of about ten to forty bps.

Oligonucleotides may be immobilized, by a number of methods known to those skilled in the art, such as laser-activated photodeprotection attachment through a phosphate group using reagents such as a nucleoside phosphoramidite or a nucleoside hydrogen phosphorate. Glass, nylon, silicon and fluorocarbon supports may be used.

Oligonucleotides may be organized into an array or arrays including all or a subset of all probes of a given length, or of sets of probes of selected lengths. Hydrophobic partitions may be used to separate probes or arrays of probes. Arrays may be designed for various applications (e.g. mapping, partial sequencing, sequencing of targeted regions for diagnostic purposes, mRNA sequencing and large scale sequencing). A specific chip may be designed to be dedicated to a particular application by selecting a combination and arrangement of probes on a substrate.

For example, 1000 immobilized probe arrays of all oligonucleotide probes 5 bases in length (each array containing 1000 distinct probes) may be constructed. A second set of 1000 oligonucleotide probes may be labeled, and one of each labeled probe may be applied to an array of immobilized probes along with a fragment to be sequenced. In this example, 1000 of the arrays would be combined in a large superarray, or "superchip." In those instances where an immobilized probe and one of the labeled probes hybridize end-to-end along a nucleic acid fragment, the two probes are joined, for example by ligation, and, after washing to remove unbound label, 10-mers complementary to the sample fragment are detected by the correlation of the presence of a label at a point in an array having an immobilized probe of known sequence to which was applied a labeled probe of known sequence. The sequence of the sample fragment is simply the sequence of the immobilized probe continued in the sequence of the labeled probe. In this way, all one million possible 10-mers may be tested by a combinatorial process which employs only 5-mers and which thus involves one thousandth of the amount of effort for oligonucleotide synthesis and quality control.

A nucleic acid sample to be sequenced may be fragmented or otherwise treated (for example, by the use of recA) to avoid hindrance to hybridization from secondary structure in the sample. The sample may be fragmented by, for example, digestion with a restriction enzyme such as the two-cutter Cvi JI, physical shearing (e.g. by ultrasound), or by NaOH treatment. The resulting fragments may be separated oby gel electrophoresis and fragments of an appropriate length, such as between about 10 bp and about 40 bp, may be extracted from the gel.

For example, a reusable Format 3 SBH array may be produced by introducing a specifically cleavable bond between the probes and then by cleaving the bond after detection. The labeled probes may be ribonucleotides or a ribonucleotide may be used as the joining base in the labeled probe so that this probe may subsequently be removed by RNAse or uracel-DNA glycosylate treatment. In addition, bonds produced by chemical ligation may be selectively cut.

Other variations include the use of modified oligonucleotides to increase specificity or efficiency, cycling hybridizations to increase the hybridization signal, for example by performing a hybridization cycle under conditions (e.g. temperature) optimally selected for a first set of labeled probes followed by hybridization under conditions optimally selected for a second set of labeled probes. Shifts in reading frame may be determined by using mixtures (preferably mixtures of equimolar amounts) of probes ending in each of the four nucleotide bases, A, T, C and G.

Within DNA, the location of certain probes may be interchangeable when determined by overlapping the sequence data, resulting in an ambiguity as to the position of the partial sequence. Although the sequence information is determined by SBH, either: (i) long read length, single-pass gel sequencing at a fraction of the cost of complete gel sequencing; or (ii) comparison to related sequences, may be used to order hybridization data where such ambiguities ("branch points") occur. In addition, segments in junk DNA (which is not found un genes) may be repeated many times in tandem. Although the sequence of the segments is determined by SBH, single-pass gel sequencing may be used to determine the number of tandem repeats where tandemly-repeated segments occur. As tandem repeats occur rarely in protein-encoding portions of a gene, the gel-sequencing step will be performed only when a commercial value for the sequence is determined.

Obtaining information about the degree of hybridization exhibited for a set of only about 200 oligonucleotides probes (about 5% of the effort required for complete sequencing) defines a unique signature of each gene and may be used for sorting the cDNAs from a library to determine if the library contains multiple copies of the same gene. By such signatures, identical, similar and different cDNAs can be distinguished and inventoried.

The present invention is illustrated in the following examples. Upon consideration of the present disclosure, one of skill in the art will appreciate that many other embodiments and variations may be made in the scope of the present invention. Accordingly, it is intended that the present invention not be limited to the disclosure of the following examples.

EXAMPLE 1

Oligonucleotide Probes and Targets Suitable for SBH

In order to obtain experimental sequence data defined as a matrix of (number of fragments-close)×(number of probes), the number of probes may be reduced depending on the number of fragments used and vice versa. The optimal ratio of the two numbers is defined by the technological requirements of a particular sequencing by hybridization process.

There are two parameters which influence the choice of probe length. The first is the success in obtaining hybridization results that show the required degree of discrimination. The second is the technological feasibility of synthesis of the required number of probes.

The requirement of obtaining sufficient hybridization discrimination with practical and useful amounts of target nucleic acid limits the probe length. It is difficult to obtain a sufficient amount of hybrid with short probes, and to discriminate end mismatches with long probes. Traditionally the use of probes shorter than 11-mers in the literature, is limited to very stable probes [Estivill et al., Nucl. Acids Res. 15: 1415 (1987)] On the other hand, probes longer than 15 bases discriminate end mismatches with difficulty (Wood et al., Proc. Natl. Acad. Sci. U.S.A. 82: 1585 (1985)].

One solution for the problems of unstable probes and end mismatch discrimination is the use of a group of longer probes representing a single shorter probe in an informational sense. For example, groups of sixteen 10-mers may be used instead of single 8-mers. Every member of the group has a common core 8-mer and one of three possible variations on outer positions with two variations at each end. The probe may be represented as 5'(A, T, C, G) (A, T, C, G) Bg (A, T, C, G)3' (SEQ ID NO:1). With this type of probe one does not need to discriminate the non-informative end bases (two on 5' end, and one on 3' end) since only the internal 8-mer is read. This solution employs a higher mass amounts of probes and label in hybridization reactions.

These disadvantages are eliminated by the use of a few sets of discriminative hybridization conditions for oligomer probes as short as 6-mers.

The number of hybridization reactions is dependent on the number of discrete labelled probes. Therefore in the cases of sequencing shorter nucleic acids using a smaller number of fragments-clones than the number of oligonucleotides, it is better to use oligomers as the target and nucleic acid fragment as probes.

Target nucleic acids which have undefined sequences may be produced as a mixture of representative libraries in a phage or plasmid vector having inserts of genomic fragments of different sizes or in samples prepared by PCR. Inevitable gaps and uncertainties in alignment of sequenced fragments arise from nonrandom or repetitive sequence organization of complex genomes and difficulties in cloning poisonous sequences in *Escherichia coli*. These problems are inherent in sequencing large complex molecules using any method. Such problems may be minimized by the choice of libraries and number of subclones used for hybridization. Alternatively, such difficulties may be overcome through the use of amplified target sequences, e.g. by PCR amplification, ligation reactions, ligation-amplified reactions, etc.

Nucleic acids and methods for isolating, cloning and sequencing nucleic acids are well known to those of skill in the art. See e.g., Ausubel et al., *Current Protocols in Molecular Biology*, Vol. 1–2, John Wiley & Sons (1989); and Sambrook et al., Molecular Cloning A Laboratory Manual, 2nd Ed., Vols. 1–3, Cold Springs Harbor Press (1989), both of which are incorporated by reference herein.

SBH is a well developed technology that may be practiced by a number of methods known to those skilled in the art. Specifically, techniques related to sequencing by hybridization of the following documents is incorporated by reference herein: Drmanac et al., U.S. Pat. No. 5,202,231 (hereby incorporated by reference herein)—Issued Apr. 13, 1993; Drmanac et al., *Genetics*, 4, 114–128 (1989); Drmanac et al., *Proceedings of the First Int'l. Conf. Electrophoresis Supercomputing Human Genome* Cantor et al. eds. World Scientific Pub. Co., Singapore, 47–59 (1991); Drmanac et al., *Science* 260, 1649–1652 (1993); Lehrach et al., *Genome Analysis: Genetic and Physical Mapping*, 1, 39–81 (1990), Cold Spring Harbor Laboratory Press; Drmanac et al., *Nucl. Acids Res.*, 4691 (1986); Stevanovic et al., *Gene*, 79, 139 (1989); Panusku et al., *Mol. Biol. Evol.*, 1, 607 (1990); Nizetic et al., *Nucl. Acids Res.*, 19, 182 (1991); Drmanac et al., *J. Biomol. Struct. Dyn.*, 5, 1085 (1991); Hoheisel et al., *Mol. Gen.*, 4, 125–132 (1991); Streszoska et al., *Proc. Nat'l. Acad. Sci.* (U.S.A.), 88, 10089 (1991); Drmanac et al., *Nucl. Acids Res.*, 19, 5839 (1991); and Drmanac et al., *Int. J. Genome Res.*, 1, 59–79 (1992).

EXAMPLE 2

Preparation of a Universal Set of Probes

Two types of universal sets of probes may be prepared. The first is a complete set (or at least a noncomplementary subset) of relatively short probes, for example all 4096 (or about 2000 non-complementary) 6-mers, or all 16,384 (or about 8,000 non-complementary) 7-mers. Full noncomplementary subsets of 8-mers and longer probes are less convenient inasmuch as they include 32,000 or more probes.

A second type of probe set is selected as a small subset of probes still sufficient for reading every bp in any sequence with at least with one probe. For example, 12 of 16 dimers are sufficient. A small subset for 7-mers, 8-mers and 9-mers for sequencing double stranded DNA may be about 3000, 10,000 and 30,000 probes, respectively.

Probes may be prepared using standard chemistry with one to three non-specified (mixed A,T,C and G) or universal (e.g. M base or inosine) bases at the ends. If radiolabelling is used, probes may have an OH group at the 5' end for kinasing by radiolabelled phosphorous groups. Alternatively, probes labelled with any compatible system, such as fluorescent dyes, may be employed. Other types of probes, such as PNA (Protein Nucleic Acids)or probes containing modified bases which change duplex stability also may be used.

Probes may be stored in bar-coded multiwell plates. For small numbers of probes, 96-well plates may be used; for 10,000 or more probes, storage in 384- or 864-well plates is preferred. Stacks of 5 to 50 plates are enough to store all probes. Approximately 5 pg of a probe may be sufficient for hybridization with one DNA sample. Thus, from a small synthesis of about 50 mg per probe, ten million samples may be analyzed. If each probe is used for every third sample, and if each sample is 1000 bp in length, then over 30 billion bases (10 human genomes) may be sequenced by a set of 5,000 probes.

EXAMPLE 3

Probes Having Modified Oligonucleotides

Modified oligonucleotides may be introduced into hybridization probes and used under appropriate conditions therefor. For example, pyrimidines with a halogen at the $C^5$-position may be used to improve duplex stability by influencing base stacking. 2,6-diaminopurine may be used to provide a third hydrogen bond in base pairing with thymine, thereby thermally stabilizing DNA-duplexes. Using 2,5-diaminopurine may increase duplex stability to allow more stringent conditions for annealing, thereby improving the specificity of duplex formation, suppressing background problems and permitting the use of shorter oligomers.

The synthesis of the triphosphate versions of these modified nucleotides is disclosed by Hoheisel & Lehrach (1990).

One may also use the non-discriminatory base analogue, or universal base, as designed by Nichols et al. (1994). This new analogue, 1-(2-deoxy-D-ribfuranosyl)-3-nitropyrrole (designated M), was generated for use in oligonucleotide probes and primers for solving the design problems that arise as a result of the degeneracy of the genetic code, or when only fragmentary peptide sequence data are available. This analogue maximizes stacking while minimizing hydrogen-bonding interactions without sterically disrupting a DNA duplex.

The M nucleoside analogue was designed to maximize stacking interactions using aprotic polar substituents linked to heteroaromatic rings, enhancing intra- and inter-stand stacking interactions to lessen the role of hydrogen bonding in base-pairing specificity. Nichols et al. (1994) favored 3-nitropyrrole 2-deoxyribonucleoside because of its structural and electronic resemblance to p-nitroaniline, whose derivatives are among the smallest known intercaltors of double-stranded DNA.

The dimethoxytrityl-protected phosphoramidite of nucleoside M is also available for incorporation into nucleotides used as primers for sequencing and polymerase chain reaction (PCR). Nichols et al. (1994) showed that a substantial number of nucleotides can be replaced by M without loss of primer specificity.

A unique property of M is its ability to replace long strings of contiguous nucleosides and still yield functional sequencing primers. Sequences with three, six and nine M substitutions have all been reported to give readable sequencing ladders, and PCR with three different M-containing primers all resulted in amplification of the correct product (Nichols et al., 1994).

The ability of 3-nitropyrrole-containing oligonucleotides to function as primers strongly suggests that a duplex structure must form with complementary strands. Optical thermal profiles obtained for the oligonucleotides pairs $d(5-C_2-T_5XT_5G_2-3)$ (SEQ ID NO: 2) and $d(5-C_2A_5YA_5G2-3)$ (SEQ ID NO: 3) (where X and Y can be A, C, G, T or M) were reported to fit the normal sigmoidal pattern observed for the DNA double-to single strand transition. The Tm values of the oligonucleotides containing X M base pairs (where X was A, C, G or T, and Y was M) were reported to all fall within a 3° C. range (Nichols et al., 1994).

EXAMPLE 4

Selection and Labeling of Probes

When an array of subarrays is produced, the sets of probes to be hybridized in each of the hybridization cycles on each of the subarrays is defined. For example, a set of 384 probes may be selected from the universal set, and 96 probings may be performed in each of 4 cycles. Probes selected to be hybridized in one cycle preferably have similar G+C contents.

Selected probes for each cycle are transferred to a 96-well plate and then are labelled by kinasing or by other labeling procedures if they are not labelled (e.g. with stable fluorescent dyes) before they are stored.

On the basis of the first round of hybridizations, a new set of probes may be defined for each of the subarrays for additional cycles. Some of the arrays may not be used in some of the cycles. For example, if only 8 of 64 patient samples exhibit a mutation and 8 probes are scored first for each mutation, then all 64 probes may be scored in one cycle and 32 subarrays are not used. These unused subarrays may then be treated with hybridization buffer to prevent drying of the filters.

Probes may be retrieved from the storing plates by any convenient approach, such as a single channel pipetting device, or a robotic station, such as a Beckman Biomek 1000 (Beckman Instruments, Fullerton, Calif.) or a Mega Two robot (Megamation, Lawrenceville, N.J.). A robotic station may be integrated with data analysis programs and probe managing programs. Outputs of these programs may be inputs for one or more robotic stations.

Probes may be retrieved one by one and added to subarrays covered by hybridization buffer. It is preferred that retrieved probes be placed in a new plate and labelled or mixed with hybridization buffer. The preferred method of retrieval is by accessing stored plates one by one and pipetting (or transferring by metal pins) a sufficient amount of each selected probe from each plate to specific wells in an intermediary plate. An array of individually addressable pipettes or pins may be used to speed up the retrieval process.

EXAMPLE 5

Preparation of Labeled Probes

The oligonucleotide probes may be prepared by automated synthesis, which is routine to those of skill in the art, for example, using and Applied Biosystems system. Alternatively, probes may be prepared using Genosys Biotechnologies Inc. Methods using stacks of porous Teflon wafers.

Oligonucleotide probes may be labeled with, for example, radioactive labels ($^{35}S$, $^{32}P$, $^{33}P$, and preferably, $^{33}P$) for arrays with 100–200 um or 100–400 um spots; non-radioactive isotopes (Jacobsen et al., 1990); or fluorophores (Brumbaugh et al., 1988). All such labeling methods are routine in the art, as exemplified by the relevant sections in Sambrook et al. (1989) and by further references such as Schubert et al. (1990), Murakami et al. (1991) and Cate et al. (1991), all articles being specifically incorporated herein by reference.

In regard to radiolabelling, the common methods are end-labeling using T4 polynucleotide kinase or high specific activity labeling using Klenow or even T7 polymerase. These are described as follows.

Synthetic oligonucleotides are synthesized without a phosphate group at their 5 termini and are therefore easily labeled by transfer of the $-^{32}P$ or $-^{33}P$ from [$-^{32}P$]ATP or [$-^{33}P$]ATP using the enzyme bacteriophage T4 polynucleotide kinase. If the reaction is carried out efficiently, the specificity activity of such probes can be as high as the specific activity of the [$-^{32}P$]ATP or [$-^{33}P$]ATP itself. The reaction described below is designed to label 10 pmoles of an oligonucleotide to high specific activity. Labeling of different amounts of oligonucleotide can easily be achieved by increasing or decreasing the size of the reaction, keeping the concentrations of all components constant.

A reaction mixture would be created using 1.0 ul of oligonucleotide (10 pmoles/ul); 2.0 ul of 10× bacteriophage T4 polynucleotide kinase buffer; 5.0 ul of [$-^{32}P$]ATP or [$-^{33}P$]ATP (sp. Act. 5000 Ci/mmole; 10 mCi/ml in aqueous solution) (10 pmoles); and 11.4 ul of water. Eight (8) units (~1 ul) of bacteriophage T4 polynucleotide kinase is added to the reaction mixture mixed well, and incubated for 45 minutes at 37° C. The reaction is heated for 10 minutes at 68° C. to inactivate the bacteriophage T4 polynucleotide kinase.

The efficiency of transfer of $^{32}P$ or $^{33}P$ to the oligonucleotide and its specific activity is then determined. If the specific activity of the probe is acceptable, it is purified. If the specific activity is too low, an additional 8 units of enzyme is added and incubated for a further 30 minutes at 37° C. before heating the reaction for 10 minutes at 68° C. to inactivate the enzyme.

Purification of radiolabeled oligonucleotides can be achieved by precipitation with ethanol; precipitation with cetylpyridinium bromide; by chromatography through bio-gel P-60; or by chromatography on a Sep-Pak $C_{18}$ column.

Probes of higher specific activities can be obtained using the Klenow fragment of *E. coli.* DNA polymerase I to synthesize a strand of DNA complementary to the synthetic oligonucleotide. A short primer is hybridized to an oligonucleotide template whose sequence is the complement of the desired radiolabeled probe. The primer is then extended using the Klenow fragment of *E. coli* DNA polymerase I to incorporate [$-^{32}P$] dNTPs or [$-^{33}P$] dNTPs in a template-directed manner. After the reaction, the template and product are separated by denaturation followed by electrophoresis through a polyacrylamide gel under denaturing conditions. With this method, it is possible to generate oligonucleotide probes that contain several radioactive atoms per molecule of oligonucleotide, if desired.

To use this method, one would mix in a microfuge tube the calculated amounts of [a-32P]dNTPs or [a-33P]dNTPs necessary to achieve the desired specific activity and sufficient to allow complete synthesis of all template strands. The concentration of dNTPs should not be less than 1 uM at any stage during the reaction. Then add to the tube the appropriate amounts of primer and template DNAs, with the primer being in three- to tenfold molar excess over the template.

0.1 volume of 10× Klenow buffer would then be added and mixed well. 2–4 units of the Klenow fragment of *E. coli* DNA polymerase I would then be added per 5 ul of reaction volume, mixed and incubated for 2–3 hours at 4° C. If desired, the process of the reaction may be monitored by removing small (0.1 ul) aliquots and measuring the proportion of radioactivity that has become precipitable with 10% trichloroacetic acid (TCA).

The reaction would be diluted with an equal volume of gel-loading buffer, heated to 80° C. for 3 minutes, and then the entire sample loaded on a denaturing polyacrylamide gel. Following electrophoresis, the gel is autoradiographed, allowing the probe to be localized and removed from the gel. Various methods for fluorphobic labeling are also available, as follows. Brumbaugh et al. (1988) describe the synthesis of fluorescently labeled primers. A deoxyuridine analog with a primary amine "linker arm" of 12 atoms attached at C-5 is synthesized. Synthesis of the analog consists of derivatizing 2-deoxyuridine through organometallic intermediates to give 5 (methyl propenoyl)-2-deoxyuridine. Reaction with dimethoxytrityl-chloride produces the corresponding 5-dimethoxytrityl adduct. The methyl ester is hydrolyzed, activated, and reacted with an appropriately monoacylated alkyl diamine. After purification, the resultant linker arm nucleosides are converted to nucleoside analogs suitable for chemical oligonucleotide synthesis.

Oligonucleotides would then be made that include one or two linker arm bases by using modified phosphoridite chemistry. To a solution of 50 nmol of the linker arm oligonucleotide in 25 ul of 500 mM sodium bicarbonate (pH 9.4) is added 20 ul of 300 mM FITC in dimethyl sulfoxide. The mixture is agitated at room temperature for 6 hrs. The oligonucleotide is separated from free FITC by elution form a 1×30 cm Sephadex G-25 column with 20 mM ammonium acetate (pH 6), combining fractions in the first UV-absorbing peak.

In general, fluorescent labeling of an oligonucleotide as it s 5-end initially involved two steps. First, a N-protected aminoalkyl phosphoramidite derivative is added to the 5-end of an oligonucleotide during automated DNA synthesis. After removal of all protecting groups, the NHS ester of an appropriate fluorescent dye is coupled to the 5-amino group overnight followed by purification of the labeled oligonucleotide from the excess of dye using reverse phase HPLC or PAGE.

Schubert et al. (1990) described the synthesis of a phosphoramidite that enables oligonucleotides labeled with fluorescein to be produced during automated DNA synthesis.

Murakami et al. also described the preparation of flurescein-labeled oligonucleotides.

Cate et al. (1991) describe the use of oligonucleotide probes directly conjugated to alkaline phosphatase in combination with a direct chemiluminescent substrate (AMPPD) to allow probe detection.

Labeled probes could readily be purchased form a variety of commercial sources, including GENSET, rather then synthesized.

EXAMPLE 6

Removal of Phosphate Groups

Both bacterial alkaline phosphatase (BAP) and calf intestinal alkaline phosphatase (CIP) catalyze the removal of 5'-phosphate residues from DNA and RNA. They are therefore appropriate for removing 5'-phosphates from DNA and/or RNA to prevent ligation and inappropriate hybridization. Phosphate removal, as described by Sambrook et al. (1989), would be performed after cutting, or otherwise shearing, the genomic DNA.

BAP is the more active of the two alkaline phosphatases, but it is also far more resistant to heat and detergents. It is therefore difficult to inhibit BAP completely at the end of dephosphorylation reactions. Proteinase K is used to digest CIP, which must be completely removed if subsequent ligations are to work efficiently. An alternative method is to inactivate the CIP by heating to 65° C. for 1 hour (or 75° C. for 10 minutes) in the presence of 5 mM EDTA (pH 8.0) and then to purify the dephosphorylated DNA by extraction with phenol:chloroform.

EXAMPLE 7

Preparation of Sequencing Chips and Arrays

A basic example is using 6-mers attached to 50 micron surfaces to give a chip with dimensions of 3×3 mm which can be combined to give an array of 20×20 cm. Another example is using 9-mer oligonucleotides attached to 10×10 microns surface to create a 9-mer chip, with dimensions of 5×5 mm. 4000 units of such chips may be used to create a 30×30 cm array. In an array in which 4,000 to 16,000 oligochips are arranged into a square array. A plate, or collection of tubes, as also depicted, may be packaged with the array as part of the sequencing kit.

The arrays may be separated physically from each other or by hydrophobic surfaces. One possible way to utilize the hydrophobic strip separation is to use technology such as the Iso-Grid Microbiology System produced by QA Laboratories, Toronto, Canada.

Hydrophobic grid membrane filters (HGMF) have been in use in analytical food microbiology for about a decade where they exhibit unique attractions of extended numerical range and automated counting of colonies. One commercially-available grid is ISO-GRID™ from QA Laboratories Ltd. (Toronto, Canada) which consists of a square (60×60 cm) of polysulfone polymer (Gelman Tuffryn HT-450, 0.45 u pore size) on which is printed a black hydrophobic ink grid consisting of 1600 (40×40) square cells. HGMF have previously been inoculated with bacterial suspensions by vacuum filtration and incubated on the differential or selective media of choice.

Because the microbial growth is confined to grid cells of known position and size on the membrane, the HGMF functions more like an MPN apparatus than a conventional plate or membrane filter. Peterkin et al. (1987) reported that these HGMFs can be used to propagate and store genomic libraries when used with a HGMF replicator. One such instrument replicates growth from each of the 1600 cells of the ISO-GRID and enables many copies of the master HGMF to be made (Peterkin et al., 1987).

Sharpe et al. (1989) also used ISO-GRID HGMF form QA Laboratories and an automated HGMF counter (MI-100 Interpreter) and RP-100 Replicator. They reported a technique for maintaining and screening many microbial cultures.

Peterkin and colleagues later described a method for screening DNA probes using the hydrophobic grid-membrane filter (Peterkin et al., 1989). These authors reported methods for effective colony hybridization directly on HGMFs. Previously, poor results had been obtained due to the low DNA binding capacity of the epoxysulfone polymer on which the HGMFs are printed. However, Peterkin et al. (1989) reported that the binding of DNA to the surface of the membrane was improved by treating the replicated and incubated HGMF with polyethyleneimine, a polycation, prior to contact with DNA. Although this early work uses cellular DNA attachment, and has a different objective to the present invention, the methodology described may be readily adapted for Format 3 SBH.

In order to identify useful sequences rapidly, Peterkin et al. (1989) used radiolabeled plasmid DNA from various clones and tested its specificity against the DNA on the prepared HGMFs. In this way, DNA from recombinant plasmids was rapidly screened by colony hybridization against 100 organisms on HGMF replicates which can be easily and reproducibly prepared.

Manipulation with small (2–3 mm) chips, and parallel execution of thousands of the reactions. The solution of the invention is to keep the chips and the probes in the corresponding arrays. In one example, chips containing 250,000 9-mers are synthesized on a silicon wafer in the form of 8×8 mM plates (15 uM/oligonucleotide, Pease et al., 1994) arrayed in 8×12 format (96 chips) with a 1 mM groove in between. Probes are added either by multichannel pipette or pin array, one probe on one chip. To score all 4000 6-mers, 42 chip arrays have to be used, either using different ones, or by reusing one set of chip arrays several times.

In the above case, using the earlier nomenclature of the application, F=9; P=6; and F+P=15. Chips may have probes of formula BxNn, where x is a number of specified bases B; and n is a number of non-specified bases, so that x=4 to 10 and n=1 to 4. To achieve more efficient hybridization, and to avoid potential influence of any support oligonucleotides, the specified bases can be surrounded by unspecified bases, thus represented by a formula such as (N)nBx(N)m (FIG. 4).

EXAMPLE 8

Preparation of Support Bound Oligonucleotides

Oligonucleotides, i.e., small nucleic acid segments, may be readily prepared by, for example, directly synthesizing the oligonucleotide by chemical means, as is commonly practiced using an automated oligonucleotide synthesizer.

Support bound oligonucleotides may be prepared by any of the methods known to those of skill in the art using any suitable support such as glass, polystyrene or Teflon. One strategy is to precisely spot oligonucleotides synthesized by standard synthesizers. Immobilization can be achieved using passive adsorption (Inouye & Hondo, 1990); using UV light (Nagata et al., 1985; Dahlen et al., 1987; Morriey & Collins, 1989) or by covalent binding of base modified DNA (Keller et al., 1988; 1989); all references being specifically incorporated herein.

Another strategy that may be employed is the use of the strong biotin-streptavidin interaction as a linker. For example, Broude et al. (1994) describe the use of Biotinylated probes, although these are duplex probes, that are immobilized on streptavidin-coated magnetic beads.

Streptavidin-coated beads may be purchased from Dynal, Oslo. Of course, this same linking chemistry is applicable to coating any surface with streptavidin. Biotinylated probes may be purchased from various sources, such as, e.g., Operon Technologies (Alameda, Calif.).

Nunc Laboratories (Naperville, Ill.) is also selling suitable material that could be used. Nunc Laboratories have developed a method by which DNA can be covalently bound to the microwell surface termed Covalink NH. CovaLink NH is a polystyrene surface grafted with secondary amino groups (>NH) that serve as bridge-heads for further covalent coupling. CovaLink Modules may be purchased from Nunc Laboratories. DNA molecules may be bound to CovaLink exclusively at the 5'-end by a phosphoramidate bond, allowing immobilization of more than 1 pmol of DNA (Rasmussen et al., 1991).

The use of CovaLink NH strips for covalent binding of DNA molecules at the 5'-end has been described (Rasmussen et al., 1991). In this technology, a phosphoramidate bond is employed (Chu et al., 1983). This is beneficial as immobilization using only a single covalent bond is preferred. The phosphoramidate bond joins the DNA to the CovaLink NH secondary amino groups that are positioned at the end of spacer arms covalently grafted onto the polystyrene surface through a 2 nm long spacer arm. To link an oligonucleotide to CovaLink NH via an phosphoramidate bond, the oligonucleotide terminus must have a 5'-end phosphate group. It is, perhaps, even possible for biotin to be covalently bound to CovaLink and then streptavidin used to bind the probes.

More specifically, the linkage method includes dissolving DNA in water (7.5 ng/ul) and denaturing for 10 min. at 95° C. and cooling on ice for 10 min. Ice-cold 0.1 M 1-methylimidazole, pH 7.0 (1-MeIm$_7$), is then added to a final concentration of 10 mM 1-MeIm$_7$. A ss DNA solution is then dispensed into CovaLink NH strips (75 ul/well) standing on ice.

Carbodiimide 0.2 M 1-ethyl-3-(3-dimethylaminopropyl) carbodiimide (EDC), dissolved in 10 mM 1-MeIm$_7$, is made fresh and 25 ul added per well. The strips are incubated for 5 hours at 50° C. After incubation the strips are washed using, e.g., Nunc-Immuno Wash; first the wells are washed 3 times, then they are soaked with washing solution for 5 min., and finally they are washed 3 times (where in the washing solution is 0.4 N NaOH, 0.25% SDS heated to 50° C.).

It is contemplated that a further suitable method for use with the present invention is that described in PCT Patent Application WO 90/03382 (Southern & Maskos), incorporated herein by reference. This method of preparing an oligonucleotide bound to a support involves attaching a nucleoside 3'-reagent through the phosphate group by a covalent phosphodiester link to aliphatic hydroxyl groups carried by the support. The oligonucleotide is then synthesized on the supported nucleoside and protecting groups removed from the synthetic oligonucleotide chain under standard conditions that do not cleave the oligonucleotide from the support. Suitable reagents include nucleoside phosphoramidite and nucleoside hydrogen phosphorate.

An on-chip strategy for the preparation of DNA probe for the preparation of DNA probe arrays may be employed. For example, addressable laser-activated photodeprotection may be employed in the chemical synthesis of oligonucleotides directly on a glass surface, as described by Fodor et al. (1991), incorporated herein by reference. Probes may also be immobilized on nylon supports as described by Van Ness et al. (1991); or linked to Teflon using the method of Duncan & Cavalier (1988); all references being specifically incorporated herein.

To link an oligonucleotide to a nylon support, as described by Van Ness et al. (1991), requires activation of the nylon surface via alkylation and selective activation of the 5'-amine of oligonucleotides with cyanuric chloride.

One particular way to prepare support bound oligonucleotides is to utilize the light-generated synthesis described by Pease et al., (1994, incorporated herein by reference). These authors used current photolithographic techniques to generate arrays of immobilized oligonucleotide probes (DNA chips). These methods, in which light is used to direct the synthesis of oligonucleotide probes in high-density, miniaturized arrays, utilize photolabile 5'-protected N-acyl-deoxynucleoside phosphoramidites, surface linker chemistry and versatile combinatorial synthesis strategies. A matrix of 256 spatially defined oligonucleotide probes may be generated in this manner and then used in the advantageous Format 3 sequencing, as described herein.

Of course, one could easily purchase a DNA chip, such as one of the light-activated chips described above, from a commercial source. In this regard, one may contact Affymetrix of Santa Clara, Calif. 95051, and Beckman.

EXAMPLE 9

Preparation of DNA Samples

DNA fragments may be prepared as clones in M13, plasmid or lambda vectors and/or prepared directly from genomic DNA or cDNA by PCR or other amplification methods. Samples may be prepared or dispensed in multi-well plates. About 100–1000 ng of DNA samples may be prepared in 2–500 ml of final volume.

EXAMPLE 10

Preparation of Nucleic Acid Fragments

The nucleic acids to be sequenced may be obtained from any appropriate source, such as cDNAs, genomic DNA, chromosomal DNA, microdissected chromosome bands, cosmid or YAC inserts, and RNA, including mRNA without any amplification steps. For example, Sambrook et al. (1989) describes three protocols for the isolation of high molecular weight DNA from mammalian cells (p. 9.14–9.23).

The nucleic acids would then be fragmented by any of the methods known to those of skill in the art including, for example, using restriction enzymes as described at 9.24–9.28 of Sambrook et al. (1989), shearing by ultrasound and NaOH treatment.

Low pressure shearing is also appropriate, as described by Schriefer et al. (1990, incorporated herein by reference). In this method, DNA samples are passed through a small French pressure cell at a variety of low to intermediate pressures. A lever device allows controlled application of low to intermediate pressures to the cell. The results of these studies indicate that low-pressure shearing is a useful alternative to sonic and enzymatic DNA fragmentation methods.

One particularly suitable way for fragmenting DNA is contemplated to be that using the two base recognition endonuclease, CviJI, described by Fitzgerald et al. (1992). These authors described an approach for the rapid fragmentation and fractionation of DNA into particular sizes that they contemplated to be suitable for shotgun cloning and sequencing. The present inventor envisions that this will also be particularly useful for generating random, but relatively small, fragments of DNA for use in the present sequencing technology.

The restriction endonuclease CviJI normally cleaves the recognition sequence PuGCPy between the G and C to leave blunt ends. Atypical reaction conditions, which alter the specificity of this enzyme (CviJI), yield a quasi-random distribution of DNA fragments form the small molecule pUC19 (2688 base pairs). Fitzgerald et al. (1992) quantitatively evaluated the randomness of this fragmentation strategy, using a CviJI digest of pUC19 that was size fractionated by a rapid gel filtration method and directly ligated, without end repair, to a lac Z minus M13 cloning vector. Sequence analysis of 76 clones showed that CviJI** restricts pyGCPy and PuGCPu, in addition to PuCGPy sites, and that new sequence data is accumulated at a rate consistent with random fragmentation.

As reported in the literature, advantages of this approach compared to sonication and agarose gel fractionation include: smaller amounts of DNA are required (0.2–0.5 ug instead of 2–5 ug); and fewer steps are involved (no preligation, end repair, chemical extraction, or agarose gel electrophoresis and elution are needed). These advantages are also proposed to be of use when preparing DNA for sequencing by Format 3.

Irrespective of the manner in which the nucleic acid fragments are obtained or prepared, it is important to denature the DNA to give single stranded pieces available for hybridization. This is achieved by incubating the DNA solution for 2–5 minutes at 80–90° C. The solution is then cooled quickly to 2° C. to prevent renaturation of the DNA fragments before they are contacted with the chip. Phosphate groups must also be removed from genomic DNA, as described in Example VI.

EXAMPLE 11

Preparation of DNA Arrays

Arrays may be prepared by spotting DNA samples on a support such as a nylon membrane. Spotting may be performed by using arrays of metal pins (the positions of which correspond to an array of wells in a microtiter plate) to repeated by transfer of about 20 nl of a DNA solution to a nylon membrane. By offset printing, a density of dots higher than the density of the wells is achieved. One to 25 dots may be accommodated in 1 $mm^2$, depending on the type of label used. By avoiding spotting in some preselected number of rows and columns, separate subsets (subarrays) may be formed. Samples in one subarray may be the same genomic segment of DNA (or the same gene) from different individuals, or may be different, overlapped genomic clones. Each of the subarrays may represent replica spotting of the same samples. In one example, a selected gene segment may be amplified from 64 patients. For each patient, the amplified gene segment may be in one 96-well plate (all 96 wells containing the same sample). A plate for each of the 64 patients is prepared. By using a 96-pin device, all samples may be spotted on one 8×12 cm membrane. Subarrays may contain 64 samples, one from each patient. Where the 96 subarrays are identical, the dot span may be 1 $mm^2$ and there may be a 1 mm space between subarrays.

Another approach is to use membranes or plates (available from NUNC, Naperville, Ill.) which may be partitioned by physical spacers e.g. a plastic grid molded over the membrane, the grid being similar to the sort of membrane applied to the bottom of multiwell plates, or hydrophobic strips. A fixed physical spacer is not preferred for imaging by exposure to flat phosphor-storage screens or x-ray films.

EXAMPLE 12

Hybridization and Scoring Process

Labeled probes may be mixed with hybridization buffer and pipetted, preferably by multichannel pipettes, to the subarrays. To prevent mixing of the probes between subarrays (if there are no hydrophobic strips or physical barriers imprinted in the membrane), a corresponding plastic, metal or ceramic grid may be firmly pressed to the membrane. Also, the volume of the buffer may be reduced to about 1 ml or less per $mm^2$. The concentration of the probes and hybridization conditions used may be as described previously except that the washing buffer may be quickly poured over the array of subarrays to allow fast dilution of probes and thus prevent significant cross-hybridization. For the same reason, a minimal concentration of the probes may be used and hybridization time extended to the maximal practical level. For DNA detection and sequencing, knowledge of a "normal" sequence allows the use of the continuous stacking interaction phenomenon to increase the signal. In addition to the labelled probe, additional unlabelled probes which hybridize back to back with a labelled one may be added in the hybridization reaction. The amount of the hybrid may be increased several times. The probes may be connected by ligation. This approach may be important for resolving DNA regions forming "compressions".

In the case of radiolabelled probes, images of the filters may be obtained, preferably by phosphorstorage technology. Fluorescent labels may be scored by CCD cameras, confocal microscopy or otherwise. In order to properly scale and integrate data from different hybridization experiments, raw signals are normalized based on the amount of target in each dot. Differences in the amount of target DNA per dot may be corrected for by dividing signals of each probe by an average signal for all probes scored on one dot. The normalized signals may be scaled, usually from 1–100, to compare data from different experiments. Also, in each subarray, several control DNAs may be used to determine an average background signal in those samples which do not contain a full match target. For samples obtained from diploid (polyploid) scores, homozygotic controls may be used to allow recognition of heterozygotes in the samples.

EXAMPLE 13

Hybridization With Oligonucleotides

Oligonucleotides were either purchased from Genosys Inc., Houston, Tex. or made on an Applied Biosystems 381A DNA synthesizer. Most of the probes used were not purified by HPLC or gel electrophoresis. For example, probes were designed to have both a single perfectly complementary target in interferon, a M13 clone containing a 921 bp Eco RI-Bgl II human B1-interferon fragment (Ohno and Tangiuchi, Proc. Natl. Acad. Sci. 74: 4370–4374 (1981)], and at least one target with an end base mismatch in M13 vector itself.

End labelling of oligonucleotides was performed as described [Maniatis et al., *Molecular Cloning: A Laboratory Manual,* Cold Spring Harbor Laboratory Cold Spring Harbor, N.Y. (1982)] in 10 ml containing T4-polynucleotide kinase (5 units Amersham), $g^{32P}$-ATP (3.3 pM, 10 mCi Amersham 3000 Ci/mM) and oligonucleotide (4 pM, 10 ng). Specific activities of the probes were 2.5–5×10 9 cpm/nM.

Single stranded DNA (2 to 4 ml in 0.5 NaOH, 1.5 M NaCl) was spotted on a Gene Screen membrane wetted with the same solution, the filters were neutralized in 0.05 M $Na_2HPO_4$ pH 6.5, baked in an oven at 80° C. for 60 min. and UV irradiated for 1 min. Then, the filters were incubated in hybridization solution (0.5 M $Na_2HPO_4$ pH 7.2, 7% sodium lauroyl sarcosine for 5 min at room temperature and placed on the surface of a plastic Petri dish. A drop of hybridization solution (10 ml, 0.5 M $Na_2HPO_4$ pH 7.2, 7% sodium lauroyl sarcosine) with a $^{32}P$ end-labeled oligomer probe at 4 nM concentration was placed over 1–6 dots per filter, overlaid with a square piece of polyethylene (approximately 1×1 cm.), and incubated in a moist chamber at the indicated temperatures for 3 hr. Hybridization was stopped by placing the filter in 6X SSC washing solution for 3×5 minute at 0° C. to remove unhybridized probe. The filter was either dried, or further washed for the indicated times and temperatures, and autoradiographed. For discrimination measurements, the dots were excised from the dried filters after autoradiography [a phosphoimager (Molecular Dynamics, Sunnyvale, Calif.) may be used] placed in liquid scintillation cocktail and counted. The uncorrected ratio of cpms for IF and M13 dots is given as D.

The conditions reported herein allow hybridization with very short oligonucleotides but ensure discriminations between matched and mismatched oligonucleotides that are complementary to and therefore bind to a target nucleic acid. Factors which influence the efficient detection of hybridization of specific short sequences based on the degree of discriminations (D) between a perfectly complementary target and an imperfectly complementary target with a single mismatch in the hybrid are defined. In experimental tests, dot blot hybridization of twenty-eight probes that were 6 to 8 nucleotides in length to two M13 clones or to model oligonucleotides bound to membrane filters was accomplished. The principles guiding the experimental procedures are given below.

Oligonucleotide hybridization to filter bound target nucleic acids only a few nucleotides longer than the probe in conditions of probe excess is a pseudo-first order reaction with respect to target concentration. This reaction is defined by:

$$S_t/S_o = e^{-kh[OP]t}$$

Wherein $S_t$ and $S_o$ are target sequence concentrations at time t and $t_0$, respectively. (OP) is probe concentration and t is temperature. The rate constant for hybrid formation, $k_h$ increases only slightly in the 0° C. to 30° C. range (Porschke and Eigen, *J. Mol. Biol.* 62: 361 (1971); Craig et al., *J. Mol. Biol.* 62: 383 (1971)]. Hybrid melting is a first order reaction with respect to hybrid concentration (here replaced by mass due to filter bound state) as shown in:

$$H_t/H_o = e^{-kmt}$$

In this equation, $H_t$ and $H_o$ are hybrid concentrations at times t and $t_o$, respectively; $k_m$ is a rate constant for hybrid melting which is dependent on temperature and salt concentration [Ikuta et al., *Nucl. Acids Res.* 15: 797 (1987); Porsclike and Eigen, *J. Mol. Biol.* 62: 361 (1971); Craig et al., J. Mol. Biol. 62: 303 (1971)]. During hybridization, which is a strand association process, the back, melting, or strand dissociation, reaction takes place as well. Thus, the amount of hybrid formed in time is result of forward and back reactions. The equilibrium may be moved towards hybrid formation by increasing probe concentration and/or decreasing temperature. However, during washing cycles in large volumes of buffer, the melting reaction is dominant and the back reaction hybridization is insignificant, since the probe is absent. This analysis indicates workable Short Oligonucleotide Hybridization (SOH) conditions call be varied for probe concentration or temperature.

D or discrimination is defined in equation four:

$$D = H_p(t_w)/H_i(t_w)$$

$H_p(t_w)$ and $H_i(t_w)$ are the amounts of hybrids remaining after a washing time, $t_w$, for the identical amounts of perfectly and imperfectly complementary duplex, respectively. For a given temperature, the discrimination D changes with the length of washing time and reaches the maximal value when $H_i = B$ which is equation five.

The background, B, represents the lowest hybridization signal detectable in the system. Since any further decrease of $H_i$ may not be examined, D increases upon continued washing. Washing past $t_w$ just decreases $H_p$ relative to B, and is seen as a decrease in D. The optimal washing time, $t_w$, for imperfect hybrids, from equation three and equation five is:

$$t_w = -ln(B/H_i(t_0))/k_{m,i}$$

Since $H_p$ is being washed for the same $t_w$, combining equations, one obtains the optimal discrimination function:

$$D = e^{ln(B/Hi(t0))km,p/km,i} X H_p(t_0)/B$$

The change of D as a function, of T is important because of the choice of an optimal washing temperature. It is obtained by substituting the Arhenius equation which is:

$$K-=Ae^{-Ea/RT}$$

into the previous equation to form the final equation:

$$D = H_p((t_0)/B X (B/H_i(t_0))^{(Ap/Ai)e(Ea,i-Ea,p)/RT};$$

Wherein B is less than $H_i(t_0)$.

Since the activation energy for perfect hybrids, $E_{a,p}$, and the activation energy for imperfect hybrids, $E_{a,i}$, can be either equal, or $E_{a,i}$ less than $E_{a,p}$ D is temperature independent, or decreases with increasing temperature, respectively. This result implies that the search for stringent temperature conditions for good discrimination in SOH is unjustified. By washing at lower temperatures, one obtains equal or better discrimination, but the time of washing exponentially increases with the decrease of temperature. Discrimination more strongly decreases with T, if $H_i(t_o)$ increases relative to $H_p(t_o)$.

D at lower temperatures depends to a higher degree on the $H_p(t_0)/B$ ratio than on the $H_p(t_0)$ ratio. This result indicates that it is better to obtain a sufficient quantity of $H_p$ in the hybridization regardless of the discrimination that can be achieved in this step. Better discrimination can then be obtained by washing, since the higher amounts of perfect hybrid allow more time for differential melting to show an effect. Similarly, using larger amounts of target nucleic acid a necessary discrimination can be obtained even with small differences between $K_{m,p}$ and $K_{m,i}$.

Extrapolated to a more complex situation than covered in this simple model, the result is that washing at lower temperatures is even more important for obtaining discrimination in the case of hybridization of a probe having many end-mismatches within a given nucleic acid target.

Using the described theoretical principles as a guide for experiments, reliable hybridizations have been obtained with probes six to eight nucleotides in length. All experiments were performed with a floating plastic sheet providing a film of hybridization solution above the filter. This procedure allows maximal reduction in the amount of probe, and thus reduced label costs in dot blot hybridizations. The high concentration of sodium lauroyl sarcosine instead of sodium lauroyl sulfate in the phosphate hybridization buffer allows dropping the reaction from room temperature down to 12° C. Similarly, the 4–6 X SSC, 10% sodium lauroyl sarcosine buffer allows hybridization at temperatures as low as 2° C. The detergent in these buffers is for obtaining tolerable background with up to 40 nM concentrations of labelled probe. Preliminary characterization of the thermal stability of short oligonucleotide hybrids was determined on a prototype octamer with 50% G+C content, i.e. probe of sequence TGCTCATG. The theoretical expectation is that this probe is among the less table octamers. Its transition enthalpy is similar to those of more stable heptamers or, even to probes 6 nucleotides in length (Bresslauer et al., Proc. Natl. Acad. Sci. U.S.A. 83: 3746 (1986)). Parameter $T_d$, the temperature at which 50% of the hybrid is melted in unit time of a minute is 18° C. The result shows that $T_d$ is 15° C. lower for the 8 bp hybrid than for an 11 bp duplex [Wallace et al., Nucleic Acids Res. 6: 3543 (1979)].

In addition to experiments with model oligonucleotides, an M13 vector was chosen as a system for a practical demonstration of short oligonucleotide hybridization. The main aim was to show useful end-mismatch discrimination with a target similar to the ones which will be used in various applications of the method of the invention. Oligonucleotide probes for the M13 model were chosen in such a way that the M13 vector itself contains the end mismatched base. Vector IF, an M13 recombinant containing a 921 bp human interferon gene insert, carries single perfectly matched target. Thus, IF has either the identical or a higher number of mismatched targets in comparison to the M13 vector itself.

Using low temperature conditions and dot blots, sufficient differences in hybridization signals were obtained between tie dot containing the perfect and the mismatched targets and the dot containing the mismatched targets only. This was true for the 6-mer oligonucleotides and was also true for the 7 and 8-mer oligonucleotides hybridized to the large IF-M13 pair of nucleic acids.

The hybridization signal depends on the amount of target available on the filter for reaction with the probe. A necessary control is to show that the difference in sign intensity is not a reflection of varying amounts of nucleic acid in the two dots. Hybridization with a probe that has the same number and kind of targets in both IF and M13 shows that there is an equal amount of DNA in the dots. Since the efficiency of hybrid formation increases with hybrid length, the signal for a duplex having six nucleotides was best detected with a high mass of oligonucleotide target bound to the filter. Due to their lower molecular weight, a larger number of oligonucleotide target molecules can be bound to a given surface area when compared to large molecules of nucleic acid that serves as target.

To measure the sensitivity of detection with unpurified DNA, various amounts of phage supernatants were spotted on the filter and hybridized with a $^{32}$P-labeled octamer. As little as 50 million unpurified phage containing no more than 0.5 ng of DNA gave a detectable signal indicating that sensitivity of the short oligonucleotide hybridization method is sufficient. Reaction time is short, adding to the practicality.

As mentioned in the theoretical section above, the equilibrium yield of hybrid depends oil probe concentration and/or temperature of reaction. For instance, the signal level for the same amount of target with 4 nM octamer at 13° C. is 3 times lower than with a probe concentration of 40 nM, and is decreased 4.5-times by raising the hybridization temperature to 25° C.

The utility of the low temperature wash for achieving maximal discrimination is demonstrated. To make the phenomenon visually obvious, 50 times more DNA was put in the M13 dot than in the IF dot using hybridization with a vector specific probe. In this way, the signal after the hybridization step with the actual probe was made stronger in the, mismatched that in the matched case. The $H_p/H_i$ ratio was 1:4. Inversion of signal intensities after prolonged washing at 7° C. was achieved without a massive loss of perfect hybrid, resulting in a ratio of 2:1. In contrast, it is impossible to achieve any discrimination at 25° C., since the matched target signal is already brought down to the background level with 2 minute washing; at the same time, the signal from the mismatched hybrid is still detectable. The loss of discrimination at 13° C. compared to 7° C. is not so great but is clearly visible. If one considers the 90 minute point at 7° C. and the 15 minute point at 13° C. when, the mismatched hybrid signal is near the background level, which represents optimal washing times for the respective conditions, it is obvious that the amount of several times greater at 7° C. than at 13° C. To illustrate this further, the time course of the change discrimination with washing of the same amount of starting hybrid at the two temperatures shows the higher maximal D at the lower temperature. These results confirm the trend in the change of D with temperature and the ratio of amounts of the two types of hybrid at the start of the washing step.

In order to show the general utility of the short oligonucleotide hybridization conditions, we have looked hybridization of 4 heptamers, 10 octamers and an additional 14 probes up to 12 nucleotides in length in our simple M13 system. These include—the nonamer GTTTTTTAA and octamer GGCAGGCG representing the two extremes of GC content. Although CG content and sequence are expected to influence the stability of short hybrids [Bresslauer et al., Proc. Natl. Acad. Sci. U.S.A. 83: 3746 (1986)], the low temperature short oligonucleotide conditions were applicable to all tested probes in achieving sufficient discrimination. Since the best discrimination value obtained with probes 13 nucleotides in length was 20, a several fold drop due to sequence variation is easily tolerated.

The M13 system has the advantage of showing the effects of target DNA complexity on the levels of discrimination. For two octamers having either none or five mismatched targets and differing in only one GC pair the observed discriminations were 18.3 and 1.7, respectively.

In order to show the utility of this method, three probes 8 nucleotides in length were tested on a collection of 51 plasmid DNA dots made from a library in Bluescript vector. One probe was present and specific for Bluescript vector but was absent in M13, while the other two probes had targets that were inserts of known sequence. This system allowed the use of hybridization negative or positive control DNAs with each probe. This probe sequence (CTCCCTTT) also had a complementary target in the interferon insert. Since the M13 dot is negative while the interferon insert in either M13 or Bluescript was positive, the hybridization is sequence specific. Similarly, probes that detect the target sequence in only one of 51 inserts, or in none of the examined inserts along with controls that confirm that hybridization would have occurred if the appropriate targets were present in the clones.

Thermal stability curves for very short oligonucleotide hybrids that are 6–8 nucleotides in length are at least 15° C. lower than for hybrids 11–12 nucleotides in length [FIG. 1 and Wallace et al., *Nucleic Acids Res.* 6: 3543–3557 (1979)]. However, performing the hybridization reaction at a low temperature and with a very practical 0.4–40 nM concentration of oligonucleotide probe allows the detection of complementary sequence in a known or unknown nucleic acid target. To determine an unknown nucleic acid sequence completely, an entire set containing 65,535 8-mer probes may be used. Sufficient amounts of nucleic acid for this purpose are present in convenient biological samples such as a few microliters of M13 culture, a plasmid prep from 10 ml of bacterial culture or a single colony of bacteria, or less than 1 ml of a standard PCR reaction.

Short oligonucleotides 6–10 nucleotides long give excellent discrimination. The relative decrease in hybrid stability with a single end mismatch is greater than for longer probes. Results with the octamer TGCTCATG support this conclusion. In the experiments, the target with a G/T end mismatch, hybridization to the target of this type of mismatch is the most stable of all other types of oligonucleotide. This discrimination achieved is the same as or greater than an internal G/T mismatch in a 19 base paired duplex greater than an internal G/T mismatch in a 19 paired duplex [Ikuta et al., Nucl. Acids res. 15: 797 (1987)]. Exploiting these discrimination properties using the described hybridization conditions for short oligonucleotide hybridization allows a very precise determination of oligonucleotide targets. In contrast to the ease of detecting discrimination between perfect and imperfect hybrids, a problem that may exist with using very short oligonucleotides is the preparation of sufficient amounts of hybrids. In practice, the need to discriminate $H_p$ and $H_i$ is aided by increasing the amount of DNA in the dot and/or the probe concentration, or by decreasing the hybridization temperature. However, higher probe concentrations usually increase background. Moreover, there are limits to the amounts of target nucleic acid that are practical to use. This problems was solved by the higher concentration of the detergent Sarcosyl which gave an effective background with 4 nM of probe. Further improvements may be effected either in the use of competitors for unspecific binding of probe to filter, or by changing the hybridization support material. Moreover, for probes having $E_a$ ess than 45 Kcal/mol (e.g. for many heptamers and a majority of hexamers, modified oligonucleotides give a more stable hybrid [Asseline, et al., *Proc. Nat'l Acad. Sci.* 81: 3297 (1984)] than their unmodified counterparts. The hybridization conditions described in this invention for short oligonucleotide hybridization using low temperatures give better discriminating for all sequences and duplex hybrid inputs. The only price paid in achieving uniformity in hybridization conditions for different sequences is an increase in washing time from minutes to up to 24 hours depending on the sequence. Moreover, the washing time can be further reduced by decreasing the salt concentration.

Although there is excellent discrimination of one matched hybrid over a mismatched hybrids, in short oligonucleotide hybridization, signals from mismatched hybrids exist, with the majority of the mismatch hybrids resulting from end mismatch. This may limit insert sizes that may be effectively examined by a probe of a certain length.

The influence of sequence complexity on discrimination cannot be ignored. However, the complexity effects are more significant when defining sequence information by short oligonucleotide hybridization for specific, nonrandom sequences, and can be overcome by using an appropriate probe to target length ratio. The length ratio is chosen to make unlikely, on statistical grounds, the occurrence of specific sequences which have a number of end-mismatches which would be able to eliminate or falsely invert discrimination. Results suggest the use of oligonucleotides 6, 7, and 8 nucleotides in length on target nucleic acid inserts shorter than 0.6, 2.5, and 10 kb, respectively.

EXAMPLE 14

DNA Sequencing

An array of subarrays allows for efficient sequencing of a small set of samples arrayed in the form of replicated subarrays; For example, 64 samples may be arrayed on a 8×8 mm subarray and 16×234 subarrays may be replicated on a 15×23 cm membrane with 1 mm wide spacers between the subarrays. Several replica membranes may be made. For example, probes from a universal set of three thousand seventy-two 7-mers may be divided in thirty-two 96-well plates and labelled by kinasing. Four membranes may be processed in parallel during one hybridization cycle. On each membrane, 384 probes may be scored. All probes may be scored in two hybridization cycles. Hybridization intensities may be scored and the sequence assembled as described below.

If a single sample subarray or subarrays contains several unknowns, especially when similar samples are used, a smaller number of probes may be sufficient if they are intelligently selected on the basis of results of previously scored probes. For example, if probe AAAAAAA is not positive, there is a small chance that any of 8 overlapping probes are positive. If AAAAAAA is positive, then two probes are usually positive. The sequencing process in this case consists of first hybridizing a subset of minimally overlapped probes to define positive anchors and then to successively select probes which confirms one of the most likely hypotheses about the order of anchors and size and type of gaps between them. In this second phase, pools of 2–10 probes may be used where each probe is selected to be positive in only one DNA sample which is different from the samples expected to be positive with other probes from the pool.

The subarray approach allows efficient implementation of probe competition (overlapped probes) or probe cooperation (continuous stacking of probes) in solving branching problems. After hybridization of a universal set of probes the sequence assembly program determines candidate sequence subfragments (SFs). For the further assembly of SFs, additional information has to be provided (from overlapped sequences of DNA fragments, similar sequences, single pass gel sequences, or from other hybridization or restriction mapping data). Competitive hybridization and continuous stacking interactions have been proposed for SF assembly. These approaches are of limited practical value for sequencing of large number of samples by SBH wherein a labelled probe is applied to a sample affixed to an array if a uniform array is used. Fortunately, analysis of small numbers of samples using replica subarrays allows efficient implementation of both approaches. On each of the replica subarrays, one branching point may be tested for one or more DNA samples using pools of probes similarly as in solving mutated sequences in different samples potted in the same subarray (see above).

If in each of 64 samples described in this example, there are about 100 branching points, and if 8 samples are analyzed in parallel in each subarray, then at least 800 subarray probings solve all branches. This means that for the 3072 basic probings an additional 800 probings (25%) are employed. More preferably, two probings are used for one branching point. If the subarrays are smaller, less additional probings are used. For example, if subarrays consist of 16 samples, 200 additional probings may be scored (6%). By using 7-mer probes ($N_{1-2}B_7N_{1-2}$) (SEQ ID NO:4; SEQ ID NO:1) and competitive or collaborative branching solving approaches or both, fragments of about 1000 bp fragments may be assembled by about 4000 probings. Furthermore, using 8-mer probes ($NB_8N$) (SEQ ID NO:4) 4 kb or longer fragments may be assembled with 12,000 probings. Gapped probes, for example, $NB_4NB_3N$ (SEQ ID NO:4) or $NB_4NB_4N$ may be used to reduce the number of branching points.

EXAMPLE 15

DNA Analysis by Transient Attachment to Subarrays of Probes and Ligation of Labelled Probes Oligonucleotide probes having an informative length of four to 40 bases are synthesized by standard chemistry and stored in tubes or in multiwell plates. Specific sets of probes comprising one to 10,000 probes are arrayed by deposition or in situ synthesis on separate supports or distinct sections of a larger support. In the last case, sections or subarrays may be separated by physical or hydrophobic barriers. The probe arrays may be prepared by in situ synthesis. A sample DNA of appropriate size is hybridized with one or more specific arrays. Many samples may be interrogated as pools at the same subarrays or independently with different subarrays within one support. Simultaneously with the sample or subsequently, a single labelled probe or a pool of labelled probes is added on each of the subarrays. If attached and labelled probes hybridize back to back on the complementary target in the sample DNA they are ligated. Occurrence of ligation will be measured by detecting a label from the probe.

This procedure is a variant of the described DNA analysis process in which DNA samples are not permanently attached to the support. Transient attachment is provided by probes fixed to the support. In this case there is no need for a target DNA array process. In addition, ligation allows detection of longer oligonucleotide sequences by combining short labelled probes with short fixed probes.

The process has several unique features. Basically, the transient attachment of the target allows its reuse. After ligation occur the target may be released and the label will stay covalently attached to the support. This feature allows cycling the target and production of detectable signal with a small quantity of the target. Under optimal conditions, targets do not need to be amplified, e.g. natural sources of the DNA samples maybe directly used for diagnostics and sequencing purposes. Targets may be released by cycling the temperature between efficient hybridization and efficient melting of duplexes. More preferably, there is no cycling. The temperature and concentrations of components may be defined to have an equilibrium between free targets and targets entered in hybrids at about 50:50% level. In this case there is a continuous production of ligated products. For different purposes different equilibrium ratios are optimal.

An electric field may be used to enhance target use. At the beginning, a horizontal field pulsing within each subarray may be employed to provide for faster target sorting. In this phase, the equilibrium is moved toward hybrid formation, and unlabelled probes may be used. After a target sorting phase, an appropriate washing (which may be helped by a vertical electric field for restricting movement of the samples) may be performed. Several cycles of discriminative hybrid melting, target harvesting by hybridization and ligation and removing of unused targets may be introduced to increase specificity. In the next step, labelled probes are added and vertical electrical pulses may be applied. By increasing temperature, an optimal free and hybridized target ratio may be achieved. The vertical electric field prevents diffusion of the sorted targets.

The subarrays of fixed probes and sets of labelled probes (specially designed or selected from a universal probe set) may be arranged in various ways to allow an efficient and flexible sequencing and diagnostics process. For example, if a short fragment (about 100–500 bp) of a bacterial genome is to be partially or completely sequenced, small arrays of probes (5–30 bases in length) designed on the bases of known sequence may be used. If interrogated with a different pool of 10 labelled probes per subarray, an array of 10 subarrays each having 10 probes, allows checking of 200 bases, assuming that only two bases connected by ligation are scored. Under the conditions where mismatches are discriminated throughout the hybrid, probes may be displaced by more than one base to cover the longer target with the same number of probes. By using long probes, the target may be interrogated directly without amplification or isolation from the rest of DNA in the sample. Also, several targets may be analyzed (screened for) in one sample simultaneously. If the obtained results indicate occurrence of a mutation (or a pathogen), additional pools of probes may be used to detect type of the mutation or subtype of pathogen. This is a desirable feature of the process which may be very cost effective in preventive diagnosis where only a small fraction of patients is expected to have an infection or mutation.

In the processes described in the examples, various detection methods may be used, for example, radiolabels, fluorescent labels, enzymes or antibodies (chemiluminescence), large molecules or particles detectable by light scattering or interferometric procedures.

EXAMPLE 16

Sequencing a Target Using Octamers and Nonamers

Data resulting from the hybridization of octamer and nonamer oligonucleotides shows that sequencing by hybridization provides an extremely high degree of accuracy. In this experiment, a known sequence was used to predict a series of contiguous overlapping component octamer and nonamer oligonucleotides.

In addition to the perfectly matching oligonucleotides, mismatch oligonucleotides, mismatch oligonucleotides wherein internal or end mismatches occur in the duplex formed by the oligonucleotide and the target were examined. In these analyses, the lowest practical temperature was used to maximize hybridization formation. Washes were accomplished at the same or lower temperatures to ensure maximal discrimination by utilizing the greater dissociation rate of mismatch versus matched oligonucleotide/target hybridization. These conditions are shown to be applicable to all sequences although the absolute hybridization yield is shown to be sequence dependent.

The least destablizing mismatch that can be postulated is a simple end mismatch, so that the test of sequencing by hybridization is the ability to discriminate perfectly matched oligonucleotide/target duplexes from end-mismatched oligonucleotide/target duplexes.

The discriminative values for 102 of 105 hybridizing oligonucleotides in a dot blot format were greater than 2 allowing a highly accurate generation of the sequence. This system also allowed an analysis of the effect of sequence on hybridization formation and hybridization instability.

On hundred base pairs of a known portion of a human-interferon genes prepared by PCR, i.e. a 100 bp target sequence, was generated with data resulting from the hybridization of 105 oligonucleotides probes of known sequence to the target nucleic acid. The oligonucleotide probes used included 72 octamer and 21 nonamer oligonucleotides whose sequence was perfectly complementary to the target. The set of 93 probes provided consecutive overlapping frames of the target sequence e displaced by one or two bases.

To evaluate the effect of mismatches, hyridization was examined for 12 additional probes that contained at least one end mismatch when hybridized to the 100 bp test target sequence. Also tested was the hybridization of twelve probes with target end-mismatched to four other control nucleic acid sequences chosen so that the 12 oligonucleotides formed perfectly matched duplex hybrids with the four control DNAs. Thus, the hybridization of internal mismatched, end-mismatched and perfectly matched duplex pairs of oligonucleotide and target were evaluated for each oligonucleotide used in the experiment. The effect of absolute DNA target concentration on the hybridization with the test octamer and nonamer oligonucleotides was determined by defining target DNA concentration by detecting hybridization of a different oligonucleotide probe to a single occurrence non-target site within the co-amplified plasmid DNA.

The results of this experiment showed that all oligonucleotides containing perfect matching complementary sequence to the target or control DNA hybridized more strongly than those oligonucleotides having mismatches. To come to this conclusion, we examined $H_p$ and D values for each probe. $H_p$ defines the amount of hybrid duplex formed between a test target and an oligonucleotide probe. By assigning values of between 0 and 10 to the hybridization obtained for the 105 probes, it was apparent that 68.5% of the 105 probes had an $H_p$ greater than 2.

Discrimination (D) values were obtained where D was defined as the ratio of signal intensities between 1) the dot containing a perfect matched duplex formed between test ligonucleotide and target or control nucleic acid and 2) the dot containing a mismatch duplex formed between the same oligonucleotide and a different site within the target or control nucleic acid. Variations in the value of D result from either 1) perturbations in the hybridization efficiency which allows visualization of signal over background, or 2) the type of mismatch found between the test ligonucleotide and the target. The D values obtained in this experiment were between 2 and 40 for 102 of the 105 oligonucleotide probes examined. Calculations of D for the group of 102 oligonucleotides as a whole showed the average D was 10.6.

There were 20 cases where oligonucleotide/target duplexes exhibited an end-mismatch. In five of these, D was greater than 10. The large D value in these cases is most likely due to hybridization destabilization caused by other than the most stable (G/T and G/A) end mismatches. The other possibility is there was an error in the sequence of either the oligonucleotides or the target.

Error in the target for probes with low $H_p$ was excluded as a possibility because such an error would have affected the hybridization of each of the other eight overlapping oligonucleotides. There was no apparent instability due to sequence mismatch for the other overlapping oligonucleotides, indicating the target sequence was correct. Error in the oligonucleotide sequence was excluded as a possibility after the hybridization of seven newly synthesized oligonucleotides was re-examined. Only 1 of the seven oligonucleotides resulted in a better D value. Low hybrid formation values may result from hybrid instability or from an inability to form hybrid duplex. An inability to form hybrid duplexes would result from either 1) self complementarity of the chosen probe or 2) target/target self hybridization. Oligonucleotide/oligonucleotide duplex formation may be favored over oligonucleotide/target hybrid duplex formation if the probe was self-complementary. Similarly, target/target association may be favored if the target was self-complementary or may form internal palindromes. In evaluating these possibilities, it was apparent from probe analysis that the questionable probes did not form hybrids with themselves. Moreover, in examining the contribution of target/target hybridization, it was determined that one of the questionable oligonucleotide probes hybridized inefficiently with two different DNAs containing the same target. The low probability that two different DNAs have a self-complementary region for the same target sequence leads to the conclusion that target/target hybridization did not contribute to low hybridization formation. Thus, these results indicate that hybrid instability and not the inability to form hybrids was the cause of the low hybrid formation observed for specific oligonucleotides. The results also indicate that low hybrid formation is due to the specific sequences of certain oligonucleotides. Moreover, the results indicate that reliable results may be obtained to generate sequences if octamer and nonamer oligonucleotides are used.

These results show that using the methods described long sequences of any specific target nucleic acid may be generated by maximal and unique overlap of constituent oligonucleotides. Such sequencing methods are dependent on the content of the individual component oligomers regardless of their frequency and their position.

The sequence which is generated using the algorithm described below is of high fidelity. The algorithm tolerates false positive signals from the hybridization dots as is indicated from the fact the sequence generated from the 105 hybridization values, which included four less reliable values, was correct. This fidelity in sequencing by hybridization is due to the "all or none" kinetics of short oligonucleotide hybridization and the difference in duplex stability that exists between perfectly matched duplexes and mismatched duplexes. The ratio of duplex stability of matched and end-mismatched duplexes increases with decreasing duplex length. Moreover, binding energy decreases with decreasing duplex length resulting in a lower hybridization efficiency. However, the results provided show that octamer hybridization allows the balancing of the factors affecting duplex stability and discrimination to produce a highly accurate method of sequencing by hybridization. Results presented in other examples show that oligonucleotides that are 6, 7, or 8 nucleotides can be effectively used to generate reliable sequence on targets that are 0.5 kb (for hexamers) 2 kb (for septamers) and 6 kb (for octamers). The sequence of long fragments may be overlapped to generate a complete genome sequence.

EXAMPLE 17

Analyzing the Data Obtained

Image files are analyzed by an image analysis program, like DOTS program (Drmanac et al., 1993), and scaled and evaluated by statistical functions included, e.g., in SCORES program (Drmanac et al. 1994). From the distribution of the signals an optimal threshold is determined for transforming signal into +/− output. From the position of the label detected, F+P nucleotide sequences from the fragments would be determined by combining the known sequences of the immobilized and labeled probes corresponding to the labeled positions. The complete nucleic acid sequence or sequence subfragments of the original molecule, such as a human chromosome, would then be assembled from the overlapping F+P sequence determined by computational deduction.

One option is to transform hybridization signals e.g., scores, into +/− output during the sequence assembly process. In this case, assembly will start with a F+P sequence with a very high score, for example F+P sequence AAAAAATTTTTT (SEQ ID NO:5). Scores of all four possible overlapping probes AAAAATTTTTA (SEQ. ID NO:6), AAAAATTTTTT (SEQ ID NO:7), AAAAATTTTTC (SEQ ID NO:8) and AAAAATTTTTG (SEQ ID NO:9) and three additional probes that are different at the beginning (TAAAAATTTTT (SEQ ID NO:10),; CAAAAATTTTT (SEQ ID NO:11),; GAAAAATTTTT (SEQ ID NO:12) are compared and three outcomes defined: (i) only the starting probe and only one of the four overlapping proves have scores that are significantly positive relatively to the other six probes, in this case the AAAAAATTTTTT (SEQ ID NO:7) sequence will be extended for one nucleotide to the right; (ii) no one probe except the starting probe has a significantly positive score, assembly will stop, e.g., the AAAAAATTTTT (SEQ ID NO:7) sequence is at the end of the DNA molecule that is sequenced; (iii) more than one significantly positive probe among the overlapped and/or other three probes is found; assembly is stopped because of the error or branching (Drmanac et al., 1989).

The process of computational deduction would employ computer programs using existing algorithms (see, e.g., Pevzner, 1989; Drmanac et al., 1991; Labat and Drmanac, 1993; each incorporated herein by reference).

If, in addition to F+P, F (space 1)P, F (space 2)P, F(space 3)P or F(space 4)P are determined, algorithms will be used to match all data sets to correct potential errors or to solve the situation where there is a branching problem (see, e.g., Drmanac et al., 1989; Bains et al., 1988; each incorporated herein by reference).

EXAMPLE 18

Conducting Sequencing by Two Step Hybridization

Following the certain examples to describe the execution of the sequencing methodology contemplated by the inventor. First, the whole chip would be hybridized with mixture of DNA as complex as 100 million of bp (one human chromosome). Guidelines for conducting hybridization can be found in papers such as Drmanac et al. (1990); Khrapko et al. (1991); and Broude et al. (1994). These articles teach the ranges of hybridization temperatures, buffers and washing steps that are appropriate for use in the initial steps of Format 3 SBH.

The present inventor particularly contemplates that hybridization is to be carried out for up to several hours in high salt concentrations at a low temperature (−2° C. to 5° C.) because of a relatively low concentration of target DNA that can be provided. For this purpose, SSC buffer is used instead of sodium phosphate buffer (Drmanac et al, 1990), which precipitates at 10° C. Washing does not have to be extensive (a few minutes) because of the second step, and can be completely eliminated when the hybridization cycling is used for the sequencing of highly complex DNA samples. The same buffer is used for hybridization and washing steps to be able to continue with the second hybridization step with labeled probes.

After proper washing using a simple robotic device on each array, e.g., a 8×8 mm array, one labeled, probe, e.g., a 6-mer, would be added. A 96-tip or 96-pin device would be used, performing this in 42 operations. Again, a range of discriminatory conditions could be employed, as previously described in the scientific literature.

The present inventor particularly contemplates the use of the following conditions. First, after adding labeled probes and incubating for several minutes only (because of the high concentration of added oligonucleotides) at a low temperature (0–5° C.), the temperature is increased to 3–10° C., depending on F+P length, and the washing buffer is added. At this time, the washing buffer used is one compatible with any ligation reaction (e.g., 100 mM salt concentration range). After adding ligase, the temperate is increased again to 15–37° C. to allow fast ligation (less than 30 min) and further discrimination of full match and mismatch hybrids.

The use of cationic detergents is also contemplated for use in Format 3 SBH, as described by Pontium & Berg (1991, incorporated herein by reference). These authors describe the use of two simple cationic detergents, dodecy- and cetyltrimethylammonium bromide (DTAB and CTAB) in DNA renaturation.

DTAB and CTAB are variants of the quaternary amine tetramethylammonium bromide (TMAB) in which one of the methyl groups is replaced by either a 12-carbon (DTAB) or a 16-carbon (CTAB) alkyl group. TMAB is the bromide salt of the tetramethylammonium ion, a reagent used in nucleic acid renaturation experiments to decrease the G-C content bias of the melting temperature. DTAB and CTAB are similar in structure to sodium dodecyl sulfate (SDS), with the replacement of the negatively charged sulfate of SDS by a positively charged quaternary amine. While SDS is commonly used in hybridization buffers to reduce non-specific binding and inhibit nucleases, it does not greatly affect the rate of renaturation.

When using a ligation process, the enzyme could be added with the labeled probes or after the proper washing step to reduce the background.

Although not previously proposed for use in any SBH method, ligase technology is well established within the field of molecular biology. For example, Hood and collegues described a ligase-mediated gene detection technique (Landegren et al., 1988), the methodology of which can be readily adapted for use in Format 3 SBH. Wu & Wallace also describe the use of bacteriophage T4 DNA ligase to join two adjacent, short synthetic olignucleotides. Their oligo ligation reactions were carried out in 50 mM Tris HCl pH 7.6, 10 mM $MgCl_2$, 1 mM ATP, 1 mM DTT, and 5% PEG. Ligation reactions were heated to 100° C. for 5–10 min followed by cooling to 0° C. prior to the addition of T4 DNA ligase (1 unit; Bethesda Research Laboratory). Most ligation reactions were carried out at 30° C. and terminated by heating to 100° C. for 5 min.

Final washing appropriate for discriminating detection of hybridized adjacent, or ligated, oligonucleotides of length (F+P), is then performed. This washing step is done in water for several minutes at 40–60° C. to wash out all the non-ligated labeled probes, and all other compounds, to maximally reduce background. Because of the covalently bound labeled oligonucleotides, detection is simplified (it does not have time and low temperature constrains).

Depending on the label used, imaging of the chips is done with different apparati. For radioactive labels, phosphor storage screen technology and PhosphorImager as a scanner may be used (Molecular Dynamics, Sunnyvale, Calif.). Chips are put in a cassette and covered by a phosphorous screen. After 1–4 hours of exposure, the screen is scanned and the image file stored at a computer hard disc. For the detection of fluorescent labels, CCD cameras and epifluorescent or confocal microscopy are used. For the chips generated directly on the pixels of a CCD camera, detection can be performed as described by Eggers et al. (1994, incorporated herein by reference).

Charge-coupled device (CCD) detectors serve as active solid supports that quantitatively detect and image the distribution of labeled target molecules in probe-based assays. These devices use the inherent characteristics of microelectronics that accommodate highly parallel assays, ultrasensitive detection, high throughput, integrated data acquisition and computation. Eggers et al. (1994) describe CCDs for use with probe-based assays, such as Format 3 SBH of the present invention, that allow quantitative assessments within seconds due to the high sensitivity and direct coupling employed.

The integrated CCD detection approach enables the detection of molecular binding events on chips. The detector rapidly generates a two-dimensional pattern that uniquely characterizes the sample. In the specific operation of the CCD-based molecular detector, distinct biological probes are immobilized directly on the pixels of a CCD or can be attached to a disposable cover slip placed on the CCD surface. The sample molecules can be labeled with radioisotope, chemiluminescent or fluorescent tags.

Upon exposure of the sample to the CCD-based probe array, photons or radioisotope decay products are emitted at the pixel locations where the sample has bound, in the case of Format 3, to two complementary probes. In turn, electron-hole pairs are generated in the silicon when the charged particles, or radiation from the labeled sample, are incident on the CCD gates. Electrons are then collected beneath adjacent CCD gates and sequentially read out on a display module. The number of photoelectrons generated at each pixel is directly proportional to the number of molecular binding events in such proximity. Consequently, molecular binding can be quantitatively determined (Eggers et al., 1994).

By placing the imaging array in proximity to the sample, the collection efficiency is improved by a factor of at least 10 over lens-based techniques such as those found in conventional CCD cameras. That is, the sample (emitter) is in near contact with the detector (imaging array), and this eliminates conventional imaging optics such as lenses and mirrors.

When radioisotopes are attached as reporter groups to the target molecules, energetic particles are detected. Several reporter groups that emit particles of varying energies have been successfully utilized with the micro-fabricated detectors, including $^{32}P$, $^{33}P$, $^{35}S$, $^{14}C$ and $^{125}L$. The higher energy particles, such as from $^{32}P$, provide the highest molecular detection sensitivity, whereas the lower energy particles, such as from $^{35}S$, provide better resolution. Hence the choice of the radioisotope reporter can be tailored as required. Once the particular radioisotope label is selected, the detection performance can be predicted by calculating the signal-to-noise ration (SNR), as described by Eggers et al. (1994).

An alternative luminescent detection procedure involves the use of fluorescent or chemiluminescent reporter groups attached to the target molecules. The fluorescent labels can be attached covalently or through interaction. Fluorescent dyes, such as ethidium bromide, with intense absorption bands in the near UV (300–350 nm) range and principal emission bands in the visible (500–650 nm) range, are most suited for the CCD devices employed since the quantum efficiency is several orders of magnitude lower at the excitation wavelength then at the fluorescent signal wavelength.

From the perspective of detecting luminescence, the poly-silicon CCD gates have the built-in capacity to filter away the contribution of incident light in the UV range, yet are very sensitive to the visible luminescence generated by the fluorescent reporter groups. Such inherently large discrimination against UV excitation enables large SNRs (greater than 100) to be achieved by the CCDs as formulated in the incorporated paper by Eggers et al. (1994).

For probe immobilization on the detector, hybridization matrices may be produced on inexpensive $SiO_2$ wafers, which are subsequently placed on the surface of the CCD following hybridization and drying. This format is economically efficient since the hybridization of the DNA is conducted on inexpensive disposable $SiO_2$ wafers, thus allowing reuse of the more expensive CCD detector. Alternatively, the probes can be immobilized directly on the CCD to create a dedicated probe matrix.

To immobilize probes upon the $SiO_2$ coating, a uniform epoxide layer is linked to the film surface, employing an epoxy-silane reagent and standard $SiO_2$ modification chemistry. Amine-modified oligonucleotide probes are then linked to the $SiO_2$ surface by means of secondary amine formation with the epoxide ring. The resulting linkage provides 17 rotatable bonds of separation between the 3 base of the oligonucleotide and the $SiO_2$ surface. To ensure complete amine deprotonation and to minimize secondary structure formation during coupling, the reaction is performed in 0.1 M KOH and incubated at 37° C. for 6 hours.

In Format 3 SBH in general, signals are scored per each of billion points. It would not be necessary to hybridize all arrays, e.g., 4000 5×5 mm, at a time and the successive use of smaller number of arrays is possible.

Cycling hybridizations are one possible method for increasing the hybridization signal. In one cycle, most of the fixed probes will hybridize with DNA fragments with tail sequences non-complementary for labeled probes. By increasing the temperature, those hybrids will be melted. In the next cycle, some of them (~0.1%) will hybridize with an appropriate DNA fragment and additional labeled probes will be ligated. In this case, there occurs a discriminative melting of DNA hybrids with mismatches for both probe sets simultaneously.

In the cycle hybridization, all components are added before the cycling starts, at the 37° C. for T4, or a higher temperature for a thermostable ligase. Then the temperature is decreased to 15–37° C. and the chip is incubated for up to 10 minutes, and then the temperature is increased to 37° C. or higher for a few minutes and then again reduced. Cycles can be repeated up to 10 times. In one variant, an optimal higher temperature (10–50° C.) can be used without cycling and longer ligation reaction can be performed (1–3 hours).

The procedure described herein allows complex chip manufacturing using standard synthesis and precise spotting of oligonucleotides because a relatively small number of oligonucleotides are necessary. For example, if all 7-mers oligos are synthesized (16384 probes), lists of 256 million 14-mers can be determined.

One important variant of the invented method is to use more than one differently labeled probe per base array. This can be executed with two purposes in mind; multiplexing to reduce number of separately hybridized arrays; or to determine a list of even longer oligosequences such as 3×6 or 3×7. In this case, if two labels are used, the specificity of the 3 consecutive oligonucleotides can be almost absolute because positive sites must have enough signals of both labels.

A further and additional variant is to use chips containing BxNy probes with y being from 1 to 4. Those chips allow sequence reading in different frames. This can also be achieved by using appropriate sets of labeled probes or both F and P probes could have some unspecified end positions (i.e., some element of terminal degeneracy). Universal bases may also be employed as part of a linker to join the probes of defined sequence to the solid support. This makes the probe more available to hybridization and makes the construct more stable. If a probe has 5 bases, one may, e.g., use 3 universal bases as a linker (FIG. 4).

EXAMPLE 19

Determining Sequence from Hybridization Data

Sequence assembly may be interrupted where ever a given overlapping (N−1) mer is duplicated two or more times. Then either of the two N-mers differing in the last nucleotide may be used in extending the sequence. This branching point limits unambiguous assembly of sequence.

Reassembling the sequence of known oligonucleotides that hybridize to the target nucleic acid to generate the complete sequence of the target nucleic acid may not be accomplished in some cases. This is because some information may be lost if the target nucleic acid is not in fragments of appropriate size in relation to the size of oligonucleotide that is used for hybridizing. The quantity of information lost is proportional to the length of a target being sequenced. However, if sufficiently short targets are used, their sequence msy be unambiguously determined.

The probable frequency of duplicated sequences that would interfere with sequence assembly which is distributed along a certain length of DNA may be calculated. This derivation requires the introduction of the definition of a parameter having to do with sequence organization: the sequence subfragment (SF). A sequence subfragment results if any part of the sequence of a target nucleic acid starts and ends with an (N−1)mer that is repeated two or more times within the target sequence. Thus, subfragments are sequences generated between two points of branching in the process of assembly of the sequences in the method of the invention. The sum of all subfragments is longer than the actual target nucleic acid because of overlapping short ends. Generally, subfragments may not be assembled in a linear order without additional information since they have shared (N−1)mers at their ends and starts. Different numbers of subfragments are obtained for each nucleic acid target depending on the number of its repeated (N−1) mers. The number depends on the value of N−1 and the length of the target.

Probability calculations can estimate the interrelationship of the two factors. If the ordering of positive N-mers is accomplished by using overlapping sequences of length N−1 or at an average distance of $A_O$, the N−1 of a fragment Lf bases long is given by equation one:

$$N_{sf}=1+A_O X K X P(K, L_f)$$

Where K greater than of =2, and $P(K, L_f)$ represents the probability of an N-mer occurring K-times on a fragment $L_f$ base long. Also, a computer program that is able to form subfragments from the content of N-mers for any given sequence is described below in Example 18.

The number of subfragments increases with the increase of lengths of fragments for a given length of probe. Obtained subfragments may not be uniquely ordered among themselves. Although not complete, this information is very useful for comparative sequence analysis and the recognition of functional sequence characteristics. This type of information may be called partial sequence. Another way of obtaining partial sequence is the use of only a subset of oligonucleotide probes of a given length.

There may be relatively good agreement between predicted sequence according to theory and a computer simulation for a random DNA sequence. For instance, for N−1=7, [using an 8-mer or groups of sixteen 10-mers of type 5' (A, T, C, G) $B_8$ (A, T, C, G) [SEQ ID NO:9] 3'] a target nucleic acid of 200 bases will have an average of three subfragments. However, because of the dispersion around the mean, a library of target nucleic acid should have inserts of 500 bp so that less than 1 in 2000 targets have more than three subfragments. Thus, in an ideal case of sequence determination of a long nucleic acid of random sequence, a representative library with sufficiently short inserts of target nucleic acid may be used. For such inserts, it is possible to reconstruct the individual target by the method of the invention. The entire sequence of a large nucleic acid is then obtained by overlapping of the defined individual insert sequences.

To reduce the need for very short fragments, e.g. 50 bases for 8-mer probes. The information contained in the overlapped fragments present in every random DNA fragmentation process like cloning, or random PCR is used. It is also possible to use pools of short physical nucleic acid fragments. Using 8-mers or 11-mers like 5' (A, T, C, G) $N_8$ (A, T, C, G)3' (SEQ ID NO:1) for sequencing 1 megabase, instead of needing 20,000 50 bp fragments only 2,100 samples are sufficient. This number consists of 700 random 7 kb clones (basic library), 1250 pools of 20 clones of 500 bp (subfragments ordering library) and 150 clones from jumping (or similar) library. The developed algorithm (see Example 18) regenerates sequence using hybridization data of these described samples.

EXAMPLE 20

Algorithm

This example describes an algorithm for generation of a long sequence written in a four letter alphabet from constituent k-tuple words in a minimal number of separate, randomly defined fragments of a starting nucleic acid sequence where K is the length of an oligonucleotide probe. The algorithm is primarily intended for use in the sequencing by hybridization (SBH) process. The algorithm is based on subfragments (SF), informative fragments (IF) and the possibility of using pools of physical nucleic sequences for defining informative fragments.

As described, subfragments may be caused by branch points in the assembly process resulting from the repetition of a K−1 oligomer sequence in a target nucleic acid. Subfragments are sequence fragments found between any two repetitive words of the length K−1 that occur in a sequence. Multiple occurrences of K−1 words are the cause of interruption of ordering the overlap of K-words in the process of sequence generation. Interruption leads to a sequence remaining in the form of subfragments. Thus, the unambiguous segments between branching points whose order is not uniquely determined are called sequence subfragments.

Informative fragments are defined as fragments of a sequence that are determined by the nearest ends of overlapped physical sequence fragments.

A certain number of physical fragments may be pooled without losing the possibility of defining informative fragments. The total length of randomly pooled fragments depends on the length of k-tuples that are used in the sequencing process.

The algorithm consists of two main units. The first part is used for generation of subfragments from the set of k-tuples contained in a sequence. Subfragments may be generated within the coding region of physical nucleic acid sequence of certain sizes, or within the informative fragments defined within long nucleic acid sequences. Both types of fragments are members of the basic library. This algorithm does not describe the determination of the content of the k-tuples of the informative fragments of the basic library, i.e. the step of preparation of informative fragments to be used in the sequence generation process.

The second part of the algorithm determines the linear order of obtained subfragments with the purpose of regenerating the complete sequence of the nucleic acid fragments of the basic library. For this purpose a second, ordering library is used, made of randomly pooled fragments of the starting sequence. The algorithm does not include the step of combining sequences of basic fragments to regenerate an entire, megabase plus sequence. This may be accomplished using the link-up of fragments of the basic library which is a prerequisite for informative fragment generation. Alternatively, it may be accomplished after generation of sequences of fragments of the basic library by this algorithm, using search for their overlap, based on the presence of common end-sequences.

The algorithm requires neither knowledge of the number of appearances of a given k-tuple in a nucleic acid sequence of the basic and ordering libraries, nor does it require the information of which k-tuple words are present on the ends of a fragment. The algorithm operates with the mixed content of k-tuples of various length. The concept of the algorithm enables operations with the k-tuple sets that contain false positive and false negative k-tuples. Only in specific cases does the content of the false k-tuples primarily influence the completeness and correctness of the generated sequence. The algorithm may be used for optimization of parameters in simulation experiments, as well as for sequence generation in the actual SBH experiments e.g. generation of the genomic DNA sequence. In optimization of parameters, the choice of the oligonucleotide probes (k-tuples) for practical and convenient fragments and/or the choice of the optimal lengths and the number of fragments for the defined probes are especially important.

This part of the algorithm has a central role in the process of the generation of the sequence from the contents of k-tuples. It is based on the unique ordering of k-tuples by means of maximal overlap. The main obstacles in sequence generation are specific repeated sequences and false positive and/or negative k-tuples. The aim of this part of the algorithm is to obtain the minimal number of the longest possible subfragments, with correct sequence. This part of the algorithm consists of one basic, and several control steps. A two-stage process is necessary since certain information can be used only after generation of all primary subfragments.

The main problem of sequence generation is obtaining a repeated sequence from word contents that by definition do not carry information on the number of occurrences of the particular k-tuples. The concept of the entire algorithm depends on the basis on which this problem is solved. In principle, there are two opposite approaches: 1) repeated sequences may be obtained at the beginning, in the process of generation of pSFs, or 2) repeated sequences can be obtained later, in the process of the final ordering of the subfragments. In the first case, pSFs contain an excess of sequences and in the second case, they contain a deficit of sequences. The first approach requires elimination of the excess sequences generated, and the second requires permitting multiple use of some of the subfragments in the process of the final assembling of the sequence.

The difference in the two approaches in the degree of strictness of the rule of unique overlap of k-tuples. The less severe rule is: k-tuple X is unambiguously maximally overlapped with k-tuple Y if and only if, the rightmost k−1 end of k-tuple X is present only on the leftmost end of k-tuple Y. This rule allows the generation of repetitive sequences and the formation of surplus sequences.

A stricter rule which is used in the second approach has an addition caveat: k-tuple X is unambiguously maximally overlapped with k-tuple Y if and only if, the rightmost K−1 end of k-tuple X is present only on the leftmost end of k-tuple Y and if the leftmost K−1 end of k-tuple Y is not present on the rightmost end of any other k-tuple. The algorithm based on the stricter rule is simpler, and is described herein.

The process of elongation of a given subfragment is stopped when the right k−1 end of the last k-tuple included is not present on the left end of any k-tuple or is present on two or more k-tuples. If it is present on only one k-tuple the second part of the rule is tested. If in addition there is a k-tuple which differs from the previously included one, the assembly of the given subfragment is terminated only on the first leftmost position. If this additional k-tuple does not exist, the conditions are met for unique k−1 overlap and a given subfragment is extended to the right by one element.

Beside the basic rule, a supplementary one is used to allow the usage of k-tuples of different lengths. The maximal overlap is the length of k−1 of the shorter k-tuple of the overlapping pair. Generation of the pSFs is performed starting from the first k-tuple from the file in which k-tuples are displayed randomly and independently from their order in a nucleic acid sequence. Thus, the first k-tuple in the file is not necessarily on the beginning of the sequence, nor on the start of the particular subfragment. The process of subfragment generation is performed by ordering the k-tuples by means of unique overlap, which is defined by the described rule. Each used k-tuple is erased from the file. At the point when there are no further k-tuples unambiguously overlapping with the last one included, the building of subfragment is terminated and the buildup of another pSF is started. Since generation of a majority of subfragments does not begin from their actual starts, the formed pSF are added to the k-tuple file and are considered as a longer k-tuple. Another possibility is to form subfragments going in both directions from the starting k-tuple. The process ends when further overlap, i.e. the extension of any of the subfragments, is not possible.

The pSFs can be divided in three groups: 1) Subfragments of the maximal length and correct sequence in cases of exact k-tuple set; 2) short subfragments, formed due to the used of the maximal and unambiguous overlap rule on the incomplete set, and/or the set with some false positive k-tuples; and 3) pSFs of an incorrect sequence. The incompleteness of the set in 2) is caused by false negative results of a hybridization experiment, as well as by using an incorrect set of k-tuples. These are formed due to the false positive and false negative k-tuples and can be: a) misconnected subfragments; b) subfragments with the wrong end; and c) false positive k-tuples which appears as false minimal subfragments.

Considering false positive k-tuples, there is the possibility for the presence of a k-tuple containing more than one wrong base or containing one wrong base somewhere in the middle, as well as the possibility for a k-tuple with a wrong base on the end. Generation of short, erroneous or misconnected subfragments is caused by the latter k-tuples. The k-tuples of the former two kinds represent wrong pSFs with length equal to k-tuple length.

In the case of one false negative k-tuple, pSFs are generated because of the impossibility of maximal overlapping. In the case of the presence of one false positive k-tuple with the wrong base on its leftmost or rightmost end, pSFs are generated because of the impossibility of unambiguous overlapping. When both false positive and false negative k-tuples with a common k−1 sequence are present in the file, pSFs are generated, and one of these pSFs contains the wrong k-tuple at the relevant end.

The process of correcting subfragments with errors in sequence and the linking of unambiguously connect pSF is performed after subfragment generation and in the process of subfragment ordering. The first step which consists of cutting the misconnected pSFs and obtaining the final subfragments by unambiguous connection of pSFs is described below.

There are two approaches for the formation of misconnected subfragments. In the first a mistake occurs when an erroneous k-tuple appears on the points of assembly of the repeated sequences of lengths k−1. In the second, the repeated sequences are shorter than k−1. These situations can occur in two variants each. In the first variant, one of the repeated sequences represents the end of a fragment. In the second variant, the repeated sequence occurs at any position within the fragment. For the first possibility, the absence of some k-tuples from the file (false negatives) is required to generate a misconnection. The second possibility requires the presence of both false negative and false positive k-tuples in the file. Considering the repetitions of k−1 sequence, the lack of only one k-tuple is sufficient when either end is repeated internally. The lack of two is needed for strictly internal repetition. The reason is that the end of a sequence can be considered informatically as an endless linear array of false negative k-tuples. From the "smaller than k−1 case", only the repeated sequence of the length of k−2, which requires two or three specific erroneous k-tuples, will be considered. It is very likely that these will be the only cases which will be detected in a real experiment, the others being much less frequent.

Recognition of the misconnected subfragments is more strictly defined when a repeated sequence does not appear at the end of the fragment. In this situation, one can detect further two subfragments, one of which contains on its leftmost, and the other on its rightmost end k−2 sequences which are also present in the misconnected subfragment. When the repeated sequence is on the end of the fragment, there is only one subfragment which contains k−2 sequence causing the mistake in subfragment formation on its leftmost or rightmost end.

The removal of misconnected subfragments by their cutting is performed according to the common rule: If the leftmost or rightmost sequence of the length of k−2 of any subfragments is present in any other subfragment, the sub-fragment is to be cut into two subfragments, each of them containing k−2 sequence. This rule does not cover rarer situations of a repeated end when there are more than one false negative k-tuple on the point of repeated k−1 sequence. Misconnected subfragments of this kind can be recognized by using the information from the overlapped fragments, or informative fragments of both the basic and ordering libraries. In addition, the misconnected subfragment will remain when two or more false negative k-tuples occur on both positions which contain the identical k−1 sequence. This is a very rare situation since it requires at least 4 specific false k-tuples. An additional rule can be introduced to cut these subfragments on sequences of length k if the given sequence can be obtained by combination of sequences shorter than k−2 from the end of one subfragment and the start of another.

By strict application of the described rule, some completeness is lost to ensure the accuracy of the output. Some of the subfragments will be cut although they are not misconnected since they fit into the pattern of a misconnected subfragment. There are several situations of this kind. For example, a fragment, beside at least two identical k−1 sequences, contains any k−2 sequence from k−1 or a fragment contains k−2 sequence repeated at least twice and at least one false negative k-tuple containing given k−2 sequence in the middle, etc.

The aim of this part of the algorithm is to reduce the number of pSFs to a minimal number of longer subfragments with correct sequence. The generation of unique longer subfragments or a complete sequence is possible in two situations. The first situation concerns the specific order of repeated k−1 words. There are cases in which some or all maximally extended pSFs (the first group of pSFs) can be uniquely ordered. For example, in fragment S-R1-a-R2-b-R1-c-R2-E where S and E are the start and end of a fragment, a, b, and c are different sequences specific to respective subfragments and R1 and R2 are two k−1 sequences that are tandemly repeated, five subfragments are generated (S-R1, R1-a-R2, R2-b-R1, R1-c-R2, and R-E). They may be ordered in two ways; the original sequence above or S-R1-c-R-b-R1-a-R-E. In contrast, in a fragment with the same number and types of repeated sequences but ordered differently, i.e. S-R1-a-R1-b-R-c-R-E, there is no other sequence which includes all subfragments. Examples of this type can be recognized only after the process of generation of pSFs. They represent the necessity for two steps in the process of pSF generation. The second situation of generation of false short subfragments on positions of nonrepeated k−1 sequences when the files contain false negative and/or positive k-tuples is more important.

The solution for both pSF groups consists of two parts. First, the false positive k-tuples appearing as the nonexisting minimal subfragments are eliminated. All k-tuple subfragments of length k which do not have an overlap on either end, of the length of longer than k-a on one end and longer than k-b on the other end, are eliminated to enable formation of the maximal number of connections. In our experiments, the values for a and b of 2 and 3, respectively, appeared to be adequate to eliminate a sufficient number of false positive k-tuples.

The merging of subfragments that can be uniquely connected is accomplished in the second step. The rule for connection is: two subfragments may be unambiguously connected if, and only if, the overlapping sequence at the relevant end or start of two subfragments is not present at the start and/or end of any other subfragment.

The exception is if one subfragment from the considered pair has the identical beginning and end. In that case connection is permitted, even if there is another subfragment with the same end present in the file. The main problem here is the precise definition of overlapping sequence. The connection is not permitted if the overlapping sequence unique for only one pair of subfragments is shorter than k−2, of it is k−2 or longer but an additional subfragment exists with the overlapping sequence of any length longer than k−4. Also, both the canonical ends of pSFs and the ends after omitting one (or few) last bases are considered as the overlapping sequences.

After this step some false positive k-tuples (as minimal subfragments) and some subfragments with a wrong end may survive. In addition, in very rare occasions where a certain number of some specific false k-tuples are simultaneously present, an erroneous connection may take place. These cases will be detected and solved in the subfragment ordering process, and in the additional control steps along with the handling of uncut "misconnected" subfragments.

The short subfragments that are obtained are of two kinds. In the common case, these subfragments may be unambiguously connected among themselves because of the distribution of repeated k−1 sequences. This may be done after the process of generation of pSFs and is a good example of the necessity for two steps in the process of pSF generation. In the case of using the file containing false positive and/or false negative k-tuples, short pSFs are obtained on the sites of nonrepeated k−1 sequences. Considering false positive k-tuples, a k-tuple may contain more than one wrong base (or containing one wrong base somewhere in the middle), as well as k-tuple on the end. Generation of short and erroneous (or misconnected) subfragments is caused by the latter k-tuples. The k-tuples of the former kind represent wrong pSFs with length equal to k-tuple length.

The aim of merging pSF part of the algorithm is the reduction of the number of pSFs to the minimal number of longer subfragments with the correct sequence. All k-tuple subfragments that do not have an overlap on either end, of the length of longer than k−a on one, and longer than k−b on the other end, are eliminated to enable the maximal number of connections. In this way, the majority of false positive k-tuples are discarded. The rule for connection is: two subfragments can be unambiguously connected if, and only if the overlapping sequence of the relevant end or start of two subfragments is not present on the start and/or end of any other subfragment. The exception is a subfragment with the identical beginning and end. In that case connection is permitted, provided that there is another subfragment with the same end present in the file. The main problem here is of precise definition of overlapping sequence. The presence of at least two specific false negative k-tuples on the points of repetition of k−1 or k−2 sequences, as well as combining of the false positive and false negative k-tuples may destroy or "mask" some overlapping sequences and can produce an unambiguous, but wrong connection of pSFs. To prevent this, completeness must be sacrificed on account of exactness: the connection is not permitted on the end-sequences shorter than k−2, and in the presence of an extra overlapping sequence longer than k−4. The overlapping sequences are defined from the end of the pSFs, or omitting one, or few last bases.

In the very rare situations, with the presence of a certain number of some specific false positive and false negative k-tuples, some subfragments with the wrong end can survive, some false positive k-tuples (as minimal subfragments) can remain, or the erroneous connection can take place. These cases are detected and solved in the subfragments ordering process, and in the additional control steps along with the handling of uncut, misconnected subfragments.

The process of ordering of subfragments is similar to the process of their generation. If one considers subfragments as longer k-tuples, ordering is performed by their unambiguous connection via overlapping ends. The informational basis for unambiguous connection is the division of subfragments generated in fragments of the basic library into groups representing segments of those fragments. The method is analogous to the biochemical solution of this problem based on hybridization with longer oligonucleotides with relevant connecting sequence. The connecting sequences are generated as subfragments using the k-tuple sets of the appropriate segments of basic library fragments. Relevant segments are defined by the fragments of the ordering library that overlap with the respective fragments of the basic library. The shortest segments are informative fragments of the ordering library. The longer ones are several neighboring informative fragments or total overlapping portions of fragments corresponding of the ordering and basic libraries. In order to decrease the number of separate samples, fragments of the ordering library are randomly pooled, and the unique k-tuple content is determined.

By using the large number of fragments in the ordering library very short segments are generated, thus reducing the chance of the multiple appearance of the k−1 sequences which are the reasons for generation of the subfragments. Furthermore, longer segments, consisting of the various regions of the given fragment of the basic library, do not contain some of the repeated k−1 sequences. In every segment a connecting sequence (a connecting subfragment) is generated for a certain pair of the subfragments from the given fragment. The process of ordering consists of three steps: (1) generation of the k-tuple contents of each segment; (2) generation of subfragments in each segment; and (3) connection of the subfragments of the segments. Primary segments are defined as significant intersections and differences of k-tuple contents of a given fragment of the basic library with the k-tuple contents of the pools of the ordering library. Secondary (shorter) segments are defined as intersections and differences of the k-tuple contents of the primary segments.

There is a problem of accumulating both false positive and negative k-tuples in both the differences and intersections. The false negative k-tuples from starting sequences accumulate in the intersections (overlapping parts), as well as false positive k-tuples occurring randomly in both sequences, but not in the relevant overlapping region. On the other hand, the majority of false positive from either of the starting sequences is not taken up into intersections. This is an example of the reduction of experimental errors from individual fragments by using information from fragments overlapping with them. The false k-tuples accumulate in the differences for another reason. The set of false negatives from the original sequences are enlarged for false positives from intersections and the set of false positives for those k-tuples which are not included in the intersection by error, i.e. are false negative in the intersection. If the starting sequences contain 10% false negative data, the primary and secondary intersections will contain 19% and 28% false negative k-tuples, respectively. On the other hand, a mathematical expectation of 77 false positives may be predicted if the basic fragment and the pools have lengths of 500 bp and 10,000 bp, respectively. However, there is a possibility of recovering most of the "lost" k-tuples and of eliminating most of the false positive k-tuples.

First, one has to determine a basic content of the k-tuples for a given segment as the intersection of a given pair of the k-tuple contents. This is followed by including all k-tuples of the starting k-tuple contents in the intersection, which contain at one end k−1 and at the other end k−+ sequences which occur at the ends of two k-tuples of the basic set. This is done before generation of the differences thus preventing the accumulation of false positives in that process. Following that, the same type of enlargement of k-tuple set is applied to differences with the distinction that the borrowing is from the intersections. All borrowed k-tuples are eliminated from the intersection files as false positives.

The intersection, i.e. a set of common k-tuples, is defined for each pair (a basic fragment) X (a pool of ordering library). If the number of k-tuples in the set is significant it is enlarged with the false negatives according to the described rule. The primary difference set is obtained by subtracting from a given basic fragment the obtained intersection set. The false negative k-tuples are appended to the difference set by borrowing from the intersection set according to the described rule and, at the same time, removed from the intersection set as false positive k-tuples. When the basic fragment is longer than the pooled fragments, this difference can represent the two separate segments which somewhat reduces its utility in further steps. The primary segments are all generated intersections and differences of pairs (a basic fragment) X (a pool of ordering library) containing the significant number of k-tuples. K-tuple sets of secondary segments are obtained by comparison of k-tuple sets of all possible pairs of primary segments. The two differences are defined from each pair which produces the intersection with the significant number of k-tuples. The majority of available information from overlapped fragments is recovered in this step so that there is little to be gained from the third round of forming intersections, and differences.

(2) Generation of the subfragments of the segments is performed identically as described for the fragments of the basic library.

(3) The method of connection of subfragments consists of sequentially determining the correctly linked pairs of subfragments among the subfragments from a given basic library fragment which have some overlapped ends. In the case of 4 relevant subfragments, two or which contain the same beginning and two having the same end, there are 4 different pairs of subfragments that can be connected. In general 2 are correct and 2 are wrong. To find correct ones, the presence of the connecting sequences of each pair is tested in the subfragments generated from all primary and secondary segments for a given basic fragment. The length and the position of the connecting sequence are chosen to avoid interference with sequences which occur by chance. They are k+2 or longer, and include at least one element 2 beside overlapping sequence in both subfragments of a given pair. The connection is permitted only if the two connecting sequences are found and the remaining two do not exist. The two linked subfragments replace former subfragments in the file and the process is cyclically repeated.

Repeated sequences are generated in this step. This means that some subfragments are included in linked subfragments more than once. They will be recognized by finding the relevant connecting sequence which engages one subfragment in connection with two different subfragments.

The recognition of misconnected subfragments generated in the processes of building pSFs and merging pSFs into longer subfragments is based on testing whether the sequences of subfragments from a given basic fragment exist in the sequences of subfragments generated in the segments for the fragment. The sequences from an incorrectly connected position will not be found indicating the misconnected subfragments.

Beside the described three steps in ordering of subfragments some additional control steps or steps applicable to specific sequences will be necessary for the generation of more complete sequence without mistakes.

The determination of which subfragment belongs to which segment is performed b comparison of contents of k-tuples in segments and subfragments. Because of the errors in the k-tuple contents (due to the primary error in pools and statistical errors due to the frequency of occurrences of k-tuples) the exact partitioning of subfragments is impossible. Thus, instead of "all or none" partition, the chance of coming from the given segment (P(sf,s)) is determined for each subfragment. This possibility is the function of the lengths of k-tuples, the lengths of subfragments, the lengths of fragments of ordering library, the size of the pool, and of the percentage of false k-tuples in the file:

$$P(sf,s)=(Ck-F)/Lsf,$$

where Lsf is the length of subfragment, Ck is the number of common k-tuples for a given subfragment/segment pair, and F is the parameter that includes relations between lengths of k-tuples, fragments of basic library, the size of the pool, and the error percentage.

Subfragments attributed to a particular segment are treated as redundant short pSFs and are submitted to a process of unambiguous connection. The definition of unambiguous connection is slightly different in this case, since it is based on a probability that subfragments with overlapping end(s) belong to the segment considered. Besides, the accuracy of unambiguous connection is controlled by following the connection of these subfragments in other segments. After the connection in different segments, all of the obtained subfragments are merged together, shorter subfragments included within longer ones are eliminated, and the remaining ones are submitted to the ordinary connecting process. If the sequence is not regenerated completely, the process of partition and connection of subfragments is repeated with the same or less severe criterions of probability of belonging to the particular segment, followed by unambiguous connection.

Using severe criteria for defining unambiguous overlap, some information is not used. Instead of a complete sequence, several subfragments that define a number of possibilities for a given fragment are obtained. Using less severe criteria an accurate and complete sequence is generated. In a certain number of situations, e.g. an erroneous connection, it is possible to generate a complete, but an incorrect sequence, or to generate "monster" subfragments with no connection among them. Thus, for each fragment of the basic library one obtains: a) several possible solutions where one is correct and b) the most probable correct solution. Also, in a very small number of cases, due to the mistake in the subfragment generation process or due to the specific ratio of the probabilities of belonging, no unambiguous solution is generated or one, the most probable solution. These cases remain as incomplete sequences, or the unambiguous solution is obtained by comparing these data with other, overlapped fragments of basic library.

The described algorithm was tested on a randomly generated, 50 kb sequence, containing 40% GC to simulate the GC content of the human genome. In the middle part of this sequence were inserted various All, and some other repetitive sequences, of a total length of about 4 kb. To simulate an in vitro SBH experiment, the following operations were performed to prepare appropriate data.

Positions of sixty 5 kb overlapping "clones" were randomly defined, to simulate preparation of a basic library:

Positions of one thousand 500 bp "clones" were randomly determined to simulate making the ordering library. These fragments were extracted from the sequence. Random pools of 20 fragments were made, and k-tuple sets of pools were determined and stored on the hard disk. These data are used in the subfragment ordering phase: For the same density of clones 4 million clones in basic library and 3 million clones in ordering library are used for the entire human genome. The total number of 7 million clones is several fold smaller than the number of clones a few kb long for random cloning of almost all of genomic DNA and sequencing by a gel-based method.

From the data on the starts and ends of 5 kb fragments, 117 "informative fragments" were determined to be in the sequence. This was followed by determination of sets of overlapping k-tuples of which the single "informative fragment" consist. Only the subset of k-tuples matching a predetermined list were used. The list contained 65% 8-mers, 30% 9-mers, and 5% 10–12-mers. Processes of generation and the ordering of subfragments were performed on these data.

The testing of the algorithm was performed on the simulated data in two experiments. The sequence of 50 informative fragments was regenerated with the 100% correct data set (over 20,000 bp), and 26 informative fragments (about 10,000 bp) with 10% false k-tuples (5% positive and 5% negative ones).

In the first experiment, all subfragments were correct and in only one out of 50 informative fragments the sequence was not completely regenerated but remained in the form of 5 subfragments. The analysis of positions of overlapped fragments of ordering library has shown that they lack the information for the unique ordering of the 5 subfragments. The subfragments may be connected in two ways based on overlapping ends, 1-2-3-4-5 and 1-4-3-2-5. The only difference is the exchange of positions of subfragments 2 and 4. Since subfragments 2, 3, and 4 are relatively short (total of about 100 bp), the relatively greater chance existed, and occurred in this case, that none of the fragments of ordering library started or ended in the subfragment 3 region.

To simulate real sequencing, some false ("hybridization") data was included as input in a number of experiments. In oligomer hybridization experiments, under proposed conditions, the only situation producing unreliable data is the end mismatch versus full match hybridization. Therefore, in simulation only those k-tuples differing in a single element on either end from the real one were considered to be false positives. These "false" sets are made as follows. On the original set of a k-tuples of the informative fragment, a subset of 5% false positive k-tuples are added. False positive k-tuples are made by randomly picking a k-tuple from the set, copying it and altering a nucleotide on its beginning or end. This is followed by subtraction of a subset of 5% randomly chosen k-tuples. In this way the statistically expected number of the most complicated cases is generated in which the correct k-tuple is replaced with a k-tuple with the wrong base on the end.

Production of k-tuple sets as described leads to up to 10% of false data. This value varies from case to case, due to the randomness of choice of k-tuples to be copied, altered, and erased. Nevertheless, this percentage 3–4 times exceeds the amount of unreliable data in real hybridization experiments. The introduced error of 10% leads to the two fold increase in the number of subfragments both in fragments of basic library (basic library informative fragments) and in segments. About 10% of the final subfragments have a wrong base at the end as expected for the k-tuple set which contains false positives (see generation of primary subfragments). Neither the cases of misconnection of subfragments nor subfragments with the wrong sequence were observed. In 4 informative fragments out of 26 examined in the ordering process the complete sequence was not regenerated. In all 4 cases the sequence was obtained in the form of several longer subfragments and several shorter subfragments contained in the same segment. This result shows that the algorithmic principles allow working with a large percentage of false data.

The success of the generation of the sequence from its k-tuple content may be described in terms of completeness and accuracy. In the process of generation, two particular situations can be defined: 1) Some part of the information is missing in the generated sequence, but one knows where the ambiguities are and to which type they belong, and 2) the regenerated sequence that is obtained does not match the sequence from which the k-tuple content is generated, but the mistake can not be detected. Assuming the algorithm is developed to its theoretical limits, as in the use of the exact k-tuple sets, only the first situation can take place. There the incompleteness results in a certain number of subfragments that may not be ordered unambiguously and the problem of determination of the exact length of monotonous sequences, i.e. the number of perfect tandem repeats.

With false k-tuples, incorrect sequence may be generated. The reason for mistakes does not lie in the shortcomings of the algorithm, but in the fact that a given content of k-tuples ambiguously represents the sequence that differs from the original one. One may define three classes of error, depending on the kind of the false k-tuples present in the file. False negative k-tuples (which are not accompanied with the false positives) produce "deletions". False positive k-tuples are producing "elongations (unequal crossing over)". False positives accompanied with false negatives are the reason for generation of "insertions", alone or combined with "deletions". The deletions are produced when all of the k-tuples (or their majority) between two possible starts of the subfragments are false negatives. Since every position in the sequence is defined by k k-tuples, the occurrence of the deletions in a common case requires k consecutive false negatives. (With 10% of the false negatives and k=8, this situation takes place after every 108 elements). This situation is extremely infrequent even in mammalian genome sequencing using random libraries containing ten genome equivalents.

Elongation of the end of the sequence caused by false positive k-tuples is the special case of "insertions", since the end of the sequence can be considered as the endless linear array of false negative k-tuples. One may consider a group of false positive k-tuples producing subfragments longer than one k-tuple. Situations of this kind may be detected if subfragments are generated in overlapped fragments, like random physical fragments of the ordering library. An insertion, or insertion in place of a deletion, can arise as a result of specific combinations of false positive and false negative k-tuples. In the first case, the number of consecutive false negatives is smaller than k. Both cases require several overlapping false positive k-tuples. The insertions and deletions are mostly theoretical possibilities without sizable practical repercussions since the requirements in the number and specificity of false k-tuples are simply too high.

In every other situation of not meeting the theoretical requirement of the minimal number an the kind of the false positive and/or negatives, mistakes in the k-tuples content may produce only the lesser completeness of a generated sequence.

SBH, a sample nucleic acid is sequenced by exposing the sample to a support-bound probe of known sequence and a labeled probe or probes in solution. Wherever the probes ligase is introduced into the mixture of probes and sample, such that, wherever a support has a bound probe and a labeled probe hybridized back to back along the sample, the two probes will be chemically linked by the action of the ligase. After washing, only chemically linked support-bound and labeled probes are detected by the presence of the labeled probe. By knowing the identity of the support-bound probe at a particular location in an array, and the identity of the labeled probe, a portion of the sequence of the sample may be determined by the presence of a label at a point in an array on a Format with a sample of three substrate. And not changes not working are maximally overlapping sequences of all of the ligated probe pairs, the sequence of the sample may be reconstructed. Not of the sample to be sequenced may be a nucleic acid fragment or oligonucleotide of ten base pairs ("bp"). The sample is preferably four to one thousand bases in length.

The length of the probe is a fragment less than ten bases in length, and, preferably, is between four and nine bases in length, In this way, arrays of support-bound probes may include all oligonucleotides of a given length or may include only oligonucleotides selected for a particular test. Where all oligonucleotides of a given length are used, the number of central oligonucleotides may be calculated by $4^N$ where N is the length of the probe.

EXAMPLE 21

Re-Using Sequencing Chips

When ligation is employed in the sequencing process, then the ordinary oligonucleotide chip cannot be immediately reused. The inventor contemplates that this may be overcome in various ways.

One may employ ribonucleotides for the second probe, probe P, so that this probe may subsequently be removed by RNAse treatment. RNAse treatment may utilize RNAse A an endoribonuclease that specifically attacks single-stranded RNA 3 to pyrimidine residues and cleaves the phosphate linkage to the adjacent nucleotide. The end products are pyrimidine 3 phosphates and oligonucleotides with terminal pyrimidine 3 phosphates. RNAse A works in the absence of cofactors and divalent cations.

To utilize an RNAse, one would generally incubate the chip in any appropriate RNAse-containing buffer, as described by Sambrook et al. (1989; incorporated herein by reference). The use of 30–50 ul of RNAse-containing buffer per 8×8 mm or 9×9 mm array at 37° C. for between 10 and 60 minutes is appropriate. One would then wash with hybridization buffer.

Although not widely applicable, one could also use the uracil base, as described by Craig et al. (1989), incorporated herein by reference, in specific embodiments. Destruction of the ligated probe combination, to yield a re-usable chip, would be achieved by digestion with the E. Coli repair enzyme, uracil-DNA glycosylase which removes uracil from DNA.

One could also generate a specifically cleavable bond between the probes and then cleave the bond after detection. For example, this may be achieved by chemical ligation as described by Shabarova et al., (1991) and Dolinnaya et al., (1988), both references being specifically incorporated herein by reference.

Shabarova et al. (1991) describe the condensation of oligodeoxyribo nucleotides with cyanogen bromide as a condensing agent. In their one step chemical ligation reaction, the oligonucleotides are heated to 97° C., slowly cooled to 0° C., then 1 ul 10 mM BrCN in acetonitrile is added.

Dolinnaya et al. (1988) show how to incorporate phosphoramidiate and pyrophosphate internucleotide bonds in DNA duplexes. They also use a chemical ligation method for modification of the sugar phosphate backbone of DNA, with a water-soluble carbodiimide (CDI) as a coupling agent. The selective cleavage of a phosphoamide bond involves contact with 15% $CH_3COOH$ for 5 min at 95° C. The selective cleavage of a pyrophosphate bond involves contact with a pyridine-water mixture (9:1) and freshly distilled $(CF_3CO)_2O$.

EXAMPLE 22

Diagnostics—Scoring Known Mutations or Full Gene Resequencing

In a simple case, the goal may be to discover whether selected, known mutations occur in a DNA segment. Less than 12 probes may suffice for this purpose, for example, 5 probes positive for one allele, 5 positive for the other, and 2 negative for both. Because of the small number of probes to be scored per sample, large numbers of samples may be analyzed in parallel. For example, with 12 probes in 3 hybridization cycles, 96 different genomic loci or gene segments from 64 patient may be analyzed on one 6×9 in membrane containing 12×24 subarrays each with 64 dots representing the same DNA segment from 64 patients. In this example, samples may be prepared in sixty-four 96-well plates. Each plate may represent one patient, and each well may represent one of the DNA segments to be analyzed. The samples from 64 plates may be spotted in four replicas as four quarters of the same membrane.

A set of 12 probes may be selected by single channel pipetting or by a single pin transferring device (or by an array of individually-controlled pipets or pins) for each of the 96 segments, and the selected probes may be arrayed in twelve 96-well plates. Probes may be labelled, if they are not prelabelled, and then probes from four plates may be mixed with hybridization buffer and added to the subarrays preferentially by a 96-channel pipeting device. After one hybridization cycle it is possible to strip off previously-applied probes by incubating the membrane at 37° to 55° C. in the preferably undiluted hybridization or washing buffer.

The likelihood that probes positive for one allele are positive and probes positive for the other allele are negative may be used to determine which of the two alleles is present. In this redundant scoring scheme, some level (about 10%) of errors in hybridization of each probe may be tolerated.

An incomplete set of probes may be used for scoring most of the alleles, especially if the smaller redundancy is sufficient, e.g. one or two probes which prove the presence or absence in a sample of one of the two alleles. For example, with a set of four thousand 8-mers there is a 91% chance of finding at least one positive probe for one of the two alleles for a randomly selected locus. The incomplete set of probes may be optimized to reflect G+C content and other biases in the analyzed samples.

For full gene sequencing, genes may be amplified in an appropriate number of segments. For each segment, a set of probes (about one probe per 2–4 bases) may be selected and hybridized. These probes may identify whether there is a mutation anywhere in the analyzed segments. Segments (i.e., subarrays which contain these segments) where one or more mutated sites are detected may be hybridized with additional probes to find the exact sequence at the mutated site. If a DNA sample is tested by every second 6-mer, and a mutation is localized at the position that is surrounded by positively hybridized probes TGCAAA and TATTCC and covered by three negative probes: CAAAAC, AAACTA and ACTATT, the mutated nucleotides must be A and/or C occurring in the normal sequence at that position. They may be changed by a single base mutation, or by a one or two nucleotide deletion and/or insertion between bases AA, AC or CT.

One approach is to select a probe that extends the positively hybridized probe TGCAAA for one nucleotide to the right, and which extends the probe TATTCC one nucleotide to the left. With these 8 probes (GCAAAA, GCAAAT, GCAAAC, GCAAAG and ATATTC, TTATTC, CTATTC, GTATTC) two questionable nucleotides are determined.

The most likely hypothesis about the mutation may be determined. For example, A is found to be mutated to G. There are two solutions satisfied by these results. Either replacement of A with G is the only change or there is in addition to that change an insertion of some number of bases between newly determined G and the following C. If the result with bridging probes is negative these options may then be checked first by at least one bridging probe comprising the mutated position (AAGCTA) and with an additional 8 probes: CAAAGA, GAAAGT CAAAGC, GAAAGG and ACTATT, TCTATT, CCTATT, GCTATT,I There are many other ways to select mutation-solving probes.

In the case of diploid, particular comparisons of scores for the test samples and homozygotic control may be performed to identify heterozygotes (see above). A few consecutive probes are expected to have roughly twice smaller signals if the segment covered by these probes is mutated on one of the two chromosomes.

EXAMPLE 23

Identification of Genes (Mutations) Responsible for GeneticDisorders and Other Traits Using universal sets of longer probes (8-mers or 9-mers) on immobilized arrays of samples, DNA fragments as long as 5–20 kb may be sequenced without subcloning. Furthermore, the speed of sequencing readily may be about 10 million bp/day/hybridization instrument. This performance allows for resequencing a large fraction of human genes or the human genome repeatedly from scientifically or medically interesting individuals. To resequence 50% of the human genes, about 100 million bp is checked. That may be done in a relatively short period of time at an affordable cost.

This enormous resequencing capability may be used in several ways to identify mutations and/or genes that encode for disorders or any other traits. Basically, mRNAs (which may be converted into cDNAs) from particular tissues or genomic DNA of patients with particular disorders may be used as starting materials. From both sources of DNA, separate genes or genomic fragments of appropriate length may be prepared either by cloning procedures or by in vitro amplification procedures (for example by PCR). If cloning is used, the minimal set of clones to be analyzed may be selected from the libraries before sequencing. That may be done efficiently by hybridization of a small number of probes, especially if a small number of clones longer than 5 kb is to be sorted. Cloning may increase the amount of hybridization data about two times, but does not require tens of thousands of PCR primers.

In one variant of the procedure, gene or genomic fragments may be prepared by restriction cutting with enzymes like Hga I which cuts DNA in following way: GACGC(N5')/CTGCG(N10'). Protruding ends of five bases are different for different fragments. One enzyme produces appropriate fragments for a certain number of genes. By cutting cDNA or genomic DNA with several enzymes in separate reactions, every gene of interest may be excised appropriately. In one approach, the cut DNA is fractionated by size. DNA fragments prepared in this way (and optionally treated with Exonuclease III which individually removes nucleotides from the 3' end and increases length and specificity of the ends) maybe dispensed in the tubes or in multiwell plates. From a relatively small set of DNA adapters with a common portion and a variable protruding end of appropriate length, a pair of adapters may be selected for every gene fragment that needs to be amplified. These adapters are ligated and then PCR is performed by universal primers. From 1000 adapters, a million pairs may be generated, thus a million different fragments may be specifically amplified in the identical conditions with a universal pair of primers complementary to the common end of the adapters.

If a DNA difference is found to be repeated in several patients, and that sequence change is nonsense or can change function of the corresponding protein, then the mutated gene may be responsible for the disorder. By analyzing a significant number of individuals with particular traits, functional allelic variations of particular genes could be associated by specific traits.

This approach may be used to eliminate the need for very expensive genetic mapping on extensive pedigrees and has special value when there is no such genetic data or material.

EXAMPLE 24

Scoring Single Nucleotide Polymorphisms in Genetic Mapping

Techniques disclosed in this application are appropriate for an efficient identification of genomic fragments with single nucleotide polymorphisms (SNUPs). In 10 individuals by applying the described sequencing process on a large number of genomic fragments of known sequence that may be amplified by cloning or by in vitro amplification, a sufficient number of DNA segments with SNUPs may be identified. The polymorphic fragments are further used as SNUP markers. These markers are either mapped previously (for example they represent mapped STSs) or they may be mapped through the screening procedure described below.

SNUPs may be scored in every individual from relevant families or populations by amplifying markers and arraying them in the form of the array of subarrays. Subarrays contain the same marker amplified from the analyzed individuals. For each marker, as in the diagnostics of known mutations, a set of 6 or less probes positive for one allele and 6 or less probes positive for the other allele may be selected and scored. From the significant association of one or a group of the markers with the disorder, chromosomal position of the responsible gene(s) may be determined. Because of the high throughput and low cost, thousands of markers may be scored for thousands of individuals. This amount of data allows localization of a gene at a resolution level of less than one million bp as well as localization of genes involved in polygenic diseases. Localized genes may be identified by sequencing particular regions from relevant normal and affected individuals to score a mutation(s).

PCR is preferred for amplification of markers from genomic DNA. Each of the markers require a specific pair of primers. The existing markers may be convertible or new markers may be defined which may be prepared by cutting genomic DNA by Hga I type restriction enzymes, and by ligation with a pair of adapters.

SNUP markers can be amplified or spotted as pools to reduce the number of independent amplification reactions. In this case, more probes are scored per one sample. When 4 markers are pooled and spotted on 12 replica membranes, then 48 probes (12 per marker) may be scored in 4 cycles.

EXAMPLE 25

Detection and Verification of Identity of DNA Fragments

DNA fragments generated by restriction cutting, cloning or in vitro amplification (e.g. PCR) frequently may be identified in a experiment. Identification may be performed by verifying the presence of a DNA band of specific size on gel electrophoresis. Alternatively, a specific oligonucleotide may be prepared and used to verify a DNA sample in question by hybridization. The procedure developed here allows for more efficient identification of a large number of samples without preparing a specific oligonucleotide for each fragment. A set of positive and negative probes may be selected from the universal set for each fragment on the basis of the known sequences. Probes that are selected to be positive usually are able to form one or a few overlapping groups and negative probes are spread over the whole insert.

This technology may be used for identification of STSs in the process of their mapping on the YAC clones. Each of the STSs may be tested on about 100 YAC clones or pools of YAC clones. DNAs from these 100 reactions possibly are spotted in one subarray. Different STSs may represent consecutive subarrays. In several hybridization cycles, a signature may be generated for each of the DNA samples, which signature proves or disproves existence of the particular STS in the given YAC clone with necessary confidence.

To reduce the number of independent PCR reactions or the number of independent samples for spotting several STSs may be amplified simultaneously in a reaction or PCR samples may be mixed, respectively. In this case more probes have to be scored per one dot. The pooling of STSs is independent of pooling YACs and may be used on single YACs or pools of YACs. This scheme is especially attractive when several probes labelled with different colors are hybridized together.

In addition to confirmation of the existence of a DNA fragment in a sample, the amount of DNA may be estimated using intensities of the hybridization of several separate probes or one or more pools of probes. By comparing obtained intensities with intensities for control samples having a known amount of DNA, the quantity of DNA in all spotted samples is determined simultaneously. Because only a few probes are necessary for identification of a DNA fragment, and there are N possible probes that may be used for DNA N bases long, this application does not require a large set of probes to be sufficient for identification of any DNA segment. From one thousand 8-mers, on average about 30 full matching probes may be selected for a 1000 bp fragment.

EXAMPLE 26

Identification of Infectious Disease Organisms and Their Variants

DNA-based tests for the detection of viral, bacterial, fungal and other parasitic organisms in patients are usually more reliable and less expensive than alternatives. The major advantage of DNA tests is to be able to identify specific strains and mutants, and eventually be able to apply more effective treatment. Two applications are described below.

The presence of 12 known antibiotic resistance genes in bacterial infections may be tested by amplifying these genes. The amplified products from 128 patients may be spotted in two subarrays and 24 subarrays for 12 genes may then be repeated four times on a 8×12 cm membrane. For each gene, 12 probes may be selected for positive and negative scoring. Hybridizations may be performed in 3 cycles. For these tests, a much smaller set of probes is most likely to be universal. For example, from a set of one thousand 8-mers, on average 30 probes are positive in 1000 bp fragments, and 10 positive probes are usually sufficient for a highly reliable identification. As described in Example 9, several genes may be amplified and/or spotted together and the amount of the given DNA may be determined. The amount of amplified gene may be used as an indicator of the level of infection.

Another example involves possible sequencing of one gene or the whole genome of an HIV virus. Because of rapid diversification, the virus poses many difficulties for selection of an optimal therapy. DNA fragments may be amplified from isolated viruses from up to 64 patients and resequenced by the described procedure. On the basis of the obtained sequence the optimal therapy may be selected. If there is a mixture of two virus types of which one has the basic sequence (similar to the case of heterozygotes), the mutant may be identified by quantitative comparisons of its hybridization scores with scores of other samples, especially control samples containing the basic virus type only. Scores twice as small may be obtained for three to four probes that cover the site mutated in one of the two virus types present in the sample (see above).

EXAMPLE 27

Forensic and Parental Identification

Sequence polymorphisms make an individual genomic DNA unique. This permits analysis of blood or other body fluids or tissues from a crime scene and comparison with samples from criminal suspects. A sufficient number of polymorphic sites are scored to produce a unique signature of a sample. SBH may easily score single nucleotide polymorphisms to produce such signatures.

A set of DNA fragments (10–1000) may be amplified from samples and suspects. DNAs from samples and suspects representing one fragment are spotted in one or several subarrays and each subarray may be replicated 4 times. In three cycles, 12 probes may determine the presence of allele A or B in each of the samples, including suspects, for each DNA locus. Matching the patterns of samples and suspects may lead to discovery of the suspect responsible for the crime.

The same procedure may be applicable to prove or disprove the identity of parents of a child. DNA may be prepared and polymorphic loci amplified from the child and adults; patterns of A or B alleles may be determined by hybridization for each. Comparisons of the obtained patterns, along with positive and negative controls, aide in the determination of familial relationships. In this case, only a significant portion of the alleles need match with one parent for identification. Large numbers of scored loci allow for the avoidance of statistical errors in the procedure or of masking effects of de novo mutations.

EXAMPLE 28

Assessing Genetic Diversity of Populations or Species and Biological Diversity of Ecological Niches Measuring the frequency of allelic variations on a significant number of loci (for example, several genes or entire mitochondrial DNA) permits development of different types of conclusions, such as conclusions regarding the impact of the environment on the genotypes, history and evolution of a population or its susceptibility to diseases or extinction, and others. These assessments may be performed by testing specific known alleles or by full resequencing of some loci to be able to define de novo mutations which may reveal fine variations or presence of mutagens in the environment.

Additionally, biodiversity in the microbial world may be surveyed by resequencing evolutionarily conserved DNA sequences, such as the genes for ribosomal RNAs or genes for highly conservative proteins. DNA may be prepared from the environment and particular genes amplified using primers corresponding to conservative sequences. DNA fragments may be cloned preferentially in a plasmid vector (or diluted to the level of one molecule per well in multiwell plates and then amplified in vitro). Clones prepared this way may be resequenced as described above. Two types of information are obtained. First of all, a catalogue of different species may be defined as well as the density of the individuals for each species. Another segment of information may be used to measure the influence of ecological factors or pollution on the ecosystem. It may reveal whether some species are eradicated or whether the abundance ratios among species is altered due to the pollution. The method also is applicable for sequencing DNAs from fossils.

EXAMPLE 29

Detection or Quantification of Nucleic Acid Species

DNA or RNA species may be detected and quantified by employing a probe pair including an unlabeled probe fixed to a substrate and a labeled probe in a solution. The species may be detected and quantified by exposure to the unlabeled probe in the presence of the labeled probe and ligase. Specifically, the formation of an extended probe by ligation of the labeled and unlabeled probe on the sample nucleic acid backbone is indicative of the presence of the species to be detected. Thus, the presence of label at a specific point in the array on the substrate after removing unligated labeled probe indicates the presence of a sample species while the quantity of label indicates the expression level of the species.

Alternatively, one or more unlabeled probes may be arrayed on a substrate as first members of pairs with one or more labeled probes to be introduced in solution. According to one method, multiplexing of the label on the array may be carried out by using dyes which fluoresce at distinguishable wavelengths. In this manner, a mixture of cDNAs applied to an array with pairs of labeled and unlabeled probes specific for species to be identified may be examined for the presence of and expression level of cDNA species. According to a preferred embodiment this approach may be carried out to sequence portions of cDNAs by selecting pairs of unlabeled and labeled probes pairs comprising sequences which overlap along the sequence of a cDNA to be detected.

Probes may be selected to detect the presence and quantity of particular pathogenic organisms genome by including in the composition selected probe pairs which appear in combination only in target pathogenic genome organisms. Thus, while no single probe pair may necessarily be specific for the pathogenic organism genome, the combination of pairs is. Similarly, in detecting or sequencing cDNAs, it might occur that a particular probe is not be specific for a cDNA or other type of species. Nevertheless, the presence and quantity of a particular species may be determined by a result wherein a combination of selected probes situated at distinct array locations is indicative of the presence of a particular species.

An infectious agent with about 10 kb or more of DNA may be detected using a support-bound detection chip without the use of polymerase chain reaction (PCR) or other target amplification procedures. According to other methods, the genomes of infectious agents including bacteria and viruses are assayed by amplification of a single target nucleotide sequence through PCR and detection of the presence of target by hybridization of a labelled probe specific for the target sequence. Because such an assay is specific for only a single target sequence it therefore is necessary to amplify the gene by methods such as PCR to provide sufficient target to provide a detectable signal.

According to this example, an improved method of detecting nucleotide sequences characteristic of infectious agents through a Format 3-type reaction is provided wherein a solid phase detection chip is prepared which comprises an array of multiple different immobilized oligonucleotide probes specific for the infectious agent of interest. A single dot comprising a mixture of many unlabeled probes complementary to the target nucleic acid concentrates the label specific to a species at one location thereby improving sensitivity over diffuse of single probe labeling. Such multiple probes may be of overlapping sequences of the target nucleotide sequence but may also be non-overlapping sequences as well as non-adjacent. Such probes preferably have a length of about 5 to 12 nucleotides.

A nucleic acid sample exposed to the probe array and target sequences present in the sample will hybridize with the multiple immobilized probes. A pool of multiple labeled probes selected to specifically bind to the target sequences adjacent to the immobilized probes is then applied with the sample to an array of unlabeled oligonucleotide probe mixtures. Ligase enzyme is then applied to the chip to ligate the adjacent probes on the sample. The detection chip is then washed to remove unhybridized and unligated probe and sample nucleic acids and the presence of sample nucleic acid may be determined by the presence or absence of label. This method provides reliable sample detection with about a 1000-fold reduction of molarity of the sample agent.

As a further aspect of the invention, the signal of the labelled probes may be amplified by means such as providing a common tail to the free probe which itself comprises multiple chromogenic, enzymatic or radioactive labels or which is itself susceptible to specific binding by a further probe agent which is multiply labelled. In this way, a second round of signal amplification may be carried out. Labeled or unlabeled probes may be used in a second round of amplification. In this second round of amplification, a lengthy DNA sample with multiple labels may result in an increased amplification intensity signal between 10 to 100 fold which may result in a total signal amplification of 100,000 fold. Through the use of both aspects of this example, an intensity signal approximately 100,000 fold may give a positive result of probe-DNA ligation without having to employ PCR or other amplification procedures.

According to a further aspect of the invention an array or super array may be prepared which consists of a complete set of probes, for example 4096 6-mer probes. Arrays of this type are universal in a sense that they can be used for detection or partial to complete sequencing of any nucleic acid species. Individual spots in an array may contain single probe species or mixtures of probes, for example N(1–3) B(4–6) N(1–3) (SEQ ID NO:4; SEQ ID NO:1, SEQ ID NO:13) type of mixtures that are synthesized in the single reaction (N represents all four nucleotides, B one specific nucleotide and where the associated numbers are a range of numbers of bases i.e., 1–3 means "from one to three bases".) These mixtures provide stronger signal for a nucleic acid species present at low concentration by collecting signal from different parts of the same long nucleic acid species molecule. The universal set of probes may be subdivided in many subsets which are spotted as unit arrays separated by barriers that prevent spreading of hybridization buffer with sample and labeled probe(s).

For detection of a nucleic acid species with a known sequence one or more oligonucleotide sequences comprising both unlabelled fixed and labeled probes in solution may be selected. Labeled probes are synthesized or selected from the presynthesized complete sets of, for example, 7-mers. The labeled probes are added to corresponding unit arrays of fixed probes such that a pair of fixed and labeled probes will adjacently hybridize to the target sequence such that upon administration of ligase the probes will be covalently bound.

If a unit array contains more than one fixed probe (as separated spots or within the same spot) that are positive in a given nucleic acid species all corresponding labeled probes may be mixed and added to the same unit array. The mixtures of labeled probes are even more important when mixtures of nucleic acid species are tested. One example of a complex mixture of nucleic acid species are mRNAs in one cell or tissue.

According to one embodiment of the invention unit arrays of fixed probes allow use of every possible immobilized probe with cocktails of a relatively small number of labeled probes. More complex cocktails of labeled probes may be used if a multiplex labeling scheme is implemented. Preferred multiplexing methods may use different fluorescent dyes or molecular tags that may be separated by mass spectroscopy.

Alternatively, according to a preferred embodiment of the invention, relatively short fixed probes may be selected which frequently hybridize to many nucleic acid sequences. Such short probes are used in combination with a cocktail of labeled probes which may be prepared such that at least one labeled probe corresponds to each of the fixed proves. Preferred cocktails are those in which none of the labeled probes corresponds to more than one fixed probe.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method for analyzing a target nucleic acid, comprising the steps of:

provifing an array comprising a substrate and a plurality of heterogenous mixtures of different oligonucleotide probes, wherein each of said mixtures is immobilized on the substrate at a distinct position with the array;

providing a plurality of labeled oligonucleotide probes;

contacting the target nucleic acid with the immobilized probes and the labeled probes under conditions that allow the immobilized probes and the labeled probes which form perfectly hybridized matches with the target nucleic acid to be distinguished from the immobilized probes and the labeled probes that hybridize with a one base mismatch to the target nucleic acid;

covalently joining the immobilized probes and labeled probes that hybridize adjacent to each other with a target nucleic acid molecule identifying a plurality of covalently joined immobilized probes and labeled probes; and analyzing the nucleic acid from the identified probes.

2. The method of claim 1, wherein each of said mixtures is complementary to a plurality of overlapping sites in the target nucleic acid.

3. The method of claim 2, further comprising the steps of:
denaturing the covalently joined immobilized probes and labeled probes that hybridize to said target nucleic acid; and
repeating the contacting, covalently joining, and denaturing steps.

4. The method of claim 1, wherein each of said mixtures is complementary to a plurality of adjacent sites in the target nucleic acid.

5. The method of claim 4, further comprising the steps of:
denaturing the covalently joined immobilized probes and labeled probes that hybridize to said target nucleic acid; and
repeating the contacting, covalently joining, and denaturing.

6. The method of claim 1, wherein each of said mixtures is complementary to a plurality of nonadjacent sites in the target nucleic acid.

7. The method of claim 6, further comprising the steps of:
denaturing the covalently joined immobilized probes and labeled probes that hybridize to said target acid; and
repeating the contacting, covalently joining, and denaturing.

8. The method of claim 1, wherein each labeled probe is labeled with a plurality of labels.

9. The method of claim 8, wherein the labels are selected from the group consisting of a chromogenic label, an enzymatic label, and a radioactive label.

10. The method of claim 1, further comprising the step of checking a predicted sequence for the target nucleic acid versus a sequence obtained from the covalently joined probes.

11. A method of analyzing a target nucleic acid, comprising the steps of:
providing an array comprising a substrate and a plurality of heterogenous mixtures of different oligonucleotide probes, wherein each of said mixtures is immobilized on the substrate at a distinct position within the array;
providing a plurality of free oligonucleotide probes, wherein the free probes have a common tail;
contacting the target nucleic acid with the immobilized probes and free probes under conditions that allow the immobilized probes and the free probes which form perfectly hybridized matches with the nucleic acid to be distinguished from the probes that hybridize with a one base mismatch to the target nucleic acid;
covalently joining the immobilized probes and the free probes that hybridize adjacent to each other with a target nucleic acid molecule;
covalently joining the free probes with a probe agent that is multiply labeled, wherein the probe a: gent specifically binds to the common tail of the free probe;
identifying a plurality of covalently joined immobilized probes and free probes that are covalently joined with the labeled probe agent; and
analyzing the nucleic acid from the identified probes.

12. The method of claim 11, wherein the target nucleic acid has a known sequence.

13. The method of claim 11, wherein a mixture of the probes is immobilized at a single distinct position within the array, and the target nucleic acid has a known sequence.

14. The method of claim 11, wherein the target nucleic acid has a known sequence, and further comprising the step of checking a predicted sequence for the target nucleic acid versus a sequence obtained from the covalently joined probes.

15. The method of claim 11, wherein the immobilized probe and the free probe are covalently joined so that they will act as a single longer probe for purposes of branch point analysis.

16. The method of claim 15, further comprising the step of checking a predicted sequence for the target nucleic acid versus a sequence obtained from the covalently joined probes.

17. The method of claim 1, wherein the immobilized probe and the labeled probe are covalently joined so that they will act as a single longer probe for purposes of branch point analysis.

18. A method for analyzing a target nucleic acid, comprising the steps of:
providing a substrate and a heterogenous mixture of different oligonucleotide probes, wherein the mixture is immobilized on the substrate at a distinct position within the substrate;
providing a plurality of labeled oligonucleotide probes;
contacting the target nucleic acid with the immobilized probes and the labeled probes under conditions that allow the immobilized probes and the labeled probes that form perfectly hybridized matches with the target nucleic acid to be distinguished from the immobilized probes and the labeled probes that hybridize with a one base mismatch to the target nucleic acid;
covalently joining the immobilized probes and labeled probes that hybridize adjacent to each other with a target nucleic acid molecule;
identifying a plurality of covalently joined immobilized probes and labeled probes; and
analyzing the nucleic acid from the identified probes.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (xi) SEQUENCE DESCRIPTION: SEQ ID NO:1:

NNNNNNNNNN N                                                     11

(2) INFORMATION FOR SEQ ID NO:2:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:2:

CCTTTTTNTT TTTGG                                         15

```
(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:3:

CCAAAAANAA AAAGG                                                            15

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:4:

NNNNNNNNNN                                                                  10

(2) INFORMATION FOR SEQ ID NO:5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:5:

AAAAAATTTT TT                                                               12

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:6:

AAAAATTTTT TA                                                               12

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:7:

AAAAATTTTT TT                                                               12

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO:8:

AAAAATTTTT TC                                                               12
```

-continued (2) INFORMATION FOR SEQ ID NO:9:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO:9:

AAAAATTTTT TG                                                       12

(2) INFORMATION FOR SEQ ID NO:10:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO:10:

TAAAAATTTT TT                                                       12

(2) INFORMATION FOR SEQ ID NO:11:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO:11:

CAAAAATTTT TT                                                       12

(2) INFORMATION FOR SEQ ID NO:12:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO:12:

GAAAAATTTT TT                                                       12

(2) INFORMATION FOR SEQ ID NO:13:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO:13:

NNNNNNNNNN NN                                                       12